(12) United States Patent
Thomas et al.

(10) Patent No.: US 7,757,557 B2
(45) Date of Patent: *Jul. 20, 2010

(54) ULTRASONIC DETECTION MEASUREMENT SYSTEM USING A TUNABLE DIGITAL FILTER WITH 4X INTERPOLATOR

(75) Inventors: Andrew Thomas, Westford, MA (US); Steven Besser, Framingham, MA (US); Jason Toomey, Linwood, MA (US)

(73) Assignee: Olympus NDT, Waltham, MA (US)

( * ) Notice: Subject to any disclaimer, the term of this patent is extended or adjusted under 35 U.S.C. 154(b) by 195 days.

This patent is subject to a terminal disclaimer.

(21) Appl. No.: 11/490,334

(22) Filed: Jul. 20, 2006

(65) Prior Publication Data

US 2007/0084289 A1   Apr. 19, 2007

Related U.S. Application Data

(60) Provisional application No. 60/726,776, filed on Oct. 14, 2005, provisional application No. 60/726,575, filed on Oct. 14, 2005, provisional application No. 60/726,798, filed on Oct. 14, 2005.

(51) Int. Cl.
    *G01N 29/38* (2006.01)
(52) U.S. Cl. .............................. 73/602; 73/609; 73/614
(58) Field of Classification Search ......... 310/311–317; 73/600–602; 600/437–459
    See application file for complete search history.

(56) References Cited

U.S. PATENT DOCUMENTS

| | | | |
|---|---|---|---|
| 4,497,210 A | | 2/1985 | Uchida et al. |
| 5,369,624 A | * | 11/1994 | Fukukita et al. ............. 367/103 |
| 5,406,949 A | * | 4/1995 | Yao et al. ..................... 600/457 |
| 5,490,511 A | | 2/1996 | Amemiya et al. |
| 5,544,128 A | * | 8/1996 | Kim et al. .................... 367/119 |
| 5,671,154 A | * | 9/1997 | Iizuka et al. .................. 702/39 |
| 5,722,412 A | * | 3/1998 | Pflugrath et al. ............. 600/459 |
| 5,737,238 A | * | 4/1998 | Mouradian et al. .......... 700/110 |
| 5,961,461 A | * | 10/1999 | Mo et al. ..................... 600/443 |
| 6,014,407 A | * | 1/2000 | Hunsinger et al. .......... 375/140 |
| 6,141,672 A | * | 10/2000 | Driendl et al. ............... 708/320 |

(Continued)

OTHER PUBLICATIONS

Jerry E. Purcell, Ph.D., "Multirate Filter Design—An Introduction," pp. 1-15.

(Continued)

*Primary Examiner*—Long V Le
*Assistant Examiner*—Sanjay Cattungal
(74) *Attorney, Agent, or Firm*—Ostrolenk Faber LLP

(57) ABSTRACT

An ultrasonic inspection system utilizes a tunable digital filter with 4× interpolation. The system is used for scanning objects to be tested and includes a transmit/receive device to generate a test signal and receive an echo signal. A signal processing circuit processes the echo signal with one or more analog to digital converters for converting an analog version of the echo signal to a digital echo signal in the form of streaming digital data which is stored in a memory. The data is stored at a first data rate and read out at the second, slower data rate. An averaging decimator receives and processes the data from the memory and supplies it to an IIR filter and subsequently to an FIR filter and ultimately to a box car filter to effect processing thereon which increases the perceived resolution of the data by a given factor, preferably by a factor of 4.

35 Claims, 23 Drawing Sheets

U.S. PATENT DOCUMENTS

| | | | |
|---|---|---|---|
| 6,246,774 B1 * | 6/2001 | Norris et al. | 381/104 |
| 6,474,164 B1 | 11/2002 | Mucciardi et al. | |
| 6,511,426 B1 * | 1/2003 | Hossack et al. | 600/437 |
| 6,582,372 B2 * | 6/2003 | Poland | 600/463 |
| 6,789,427 B2 | 9/2004 | Batzinger et al. | |
| 6,891,311 B2 * | 5/2005 | Phelps et al. | 310/317 |
| 6,963,733 B2 | 11/2005 | Eriksson et al. | |
| 7,088,835 B1 * | 8/2006 | Norris et al. | 381/107 |
| 7,102,434 B2 | 9/2006 | Grillo | |
| 7,206,101 B2 * | 4/2007 | Avinash | 358/3.26 |
| 2006/0173314 A1 | 8/2006 | Leblanc et al. | |

OTHER PUBLICATIONS

International Search Report and Written Opinion dated Aug. 7, 2008 relating to PCT Application No. PCT/US06/37110.

PCT Notification of Transmittal of International Search Report issued in connection with corresponding PCT application PCT/US06/036908 dated Aug. 14, 2007.

International Search Report dated Oct. 19, 2007 in connection with corresponding PCT Application No. PCT/US06/36810.

* cited by examiner

FIG: 4

ULTRASONIC DETECTION MEASUREMENT SYSTEM USING A TUNABLE DIGITAL FILTER WITH 4X INTERPOLATOR

CROSS-REFERENCE TO RELATED APPLICATIONS

This application claims the benefit and priority of U.S. Provisional patent application Ser. No. 60/726,798 filed Oct. 14, 2005 entitled ULTRASONIC FAULT DETECTION SYSTEM USING A HIGH DYNAMIC RANGE ANALOG TO DIGITAL CONVERSION SYSTEM and U.S. Provisional patent application Ser. No. 60/726,776, filed Oct. 14, 2005 entitled ULTRASONIC DETECTION MEASUREMENT SYSTEM USING A TUNABLE DIGITAL FILTER WITH 4× INTERPOLATOR, and U.S. Provisional patent application Ser. No. 60/726,575, filed Oct. 14, 2005 entitled DIGITAL TIME VARIABLE AMPLIFIER FOR NON-DESTRUCTIVE TEST INSTRUMENT, the entire disclosures of which are incorporated herein by reference.

BACKGROUND OF THE INVENTION

The present invention relates to ultrasonic detection and measurement systems utilized to detect internal structural flaws within an object or material, for example, in such crucial structures as airline wings, by transmitting ultrasonic pulses to a target object and analyzing echo signals detected from the target object. The system and method of the invention also relate generally to systems utilized for applications such as corrosion measurements, thickness measurements and the like. More particularly, the present invention relates to a tunable digital filter with a 4× interpolator which has been adapted for such systems.

The prior art of ultrasonic flaw detectors is exemplified by such products as the instant assignee's Epoch 4 Plus product. Competitive products available from General Electric are known as the USM 35X, USN 58L and USN 60 fault detection systems. In general, prior art ultrasonic flaw detectors utilize highly complex analog front ends that contain many parts which pose especially difficult problems in terms of calibration, reliability, set up time, consistency of results and optimization for specific usages and settings.

Typical prior art ultrasonic flaw detectors include a transducer which is placed against the object to be tested and which works in conjunction with numerous analog circuits such as gain calibrators, preamplifiers and attenuators, voltage gain amplifiers, and high pass and low pass analog filters that operate over many different frequency bands and which need to be carefully calibrated and maintained.

As a result, present flaw detectors present a host of problems to designers and users of such equipment, which impact their troubleshooting and repair owing to their complexity. These problems include such issues as matching input impedances seen by the transducer which changes with different gain amplifiers that are switched in and out of the signal path. This adversely impacts the frequency response and introduces various gain nonlinearities. It poses issues of calibration, as analog circuits are switched in and out of the signal path.

Another problem with existing flaw detectors is attributable to their back wall attenuation performance which impacts the ability to detect flaws that are located very near the back wall of the object being tested. This problem poses particular problems with the time varied gain function which has a limited gain range and gain rate of change in prior art devices.

Another prior art drawback ensues from the manner in which analog circuits are coupled, which results in each amplifier in the signal path having different DC offset errors that must be nulled in order to keep the input signal at the mid-point of the analog to digital converter being utilized, in order to present a signal level to the converter which matches the full amplitude scale of such converter. The error nulling processes in the prior art are therefore unreliable, particularly at high gain, due to DC baseline measurement inaccuracies caused by noise.

The intensely analog implementation of the front ends of existing flaw detectors poses further issues owing to the need to utilize the entire dynamic range of the instrument that is being utilized which creates various gain linearity calibration issues.

An ultrasonic inspection apparatus of the prior art is described in U.S. Pat. No. 5,671,154, which provides background information for the apparatus and method of the present invention. A tunable digital filter arrangement is described in U.S. Pat. No. 6,141,672.

SUMMARY OF THE INVENTION

Generally, it is an object of the present invention to provide an apparatus and method for ultrasonic inspection and measurement of objects which avoid or ameliorate the aforementioned drawbacks of the prior art.

It is a further object of the invention to provide an ultrasonic inspection apparatus and method that is implemented in simpler circuitry.

It is a further object of the present invention to provide an ultrasonic inspection apparatus and method that requires a shorter and simpler process of calibration and adjustment prior to use.

Yet another object of the invention is to provide an ultrasonic inspection apparatus and method that uses a tunable digital filter with 4× interpolation. In accordance with one embodiment of the present invention, there is provided an ultrasonic detection system for scanning objects to be tested wherein the system includes a transmit and receive device to generate a test signal and to receive a responsive echo signal. A transducer is provided which converts the test signal to an ultrasonic signal, applies the ultrasonic signal to a target object to be tested and receives an ultrasonic echo signal and produces the echo signal for the transmit and receive device. A signal processing circuit coupled with the transmit and receive device for receiving and processing the echo signal includes one or more analog to digital converters for converting an analog version of the echo signal to a digital echo signal in the form of streaming digital data at a sampling clock rate.

A memory is provided in which the streaming data is stored at the first data rate and for which it can be read out at a different, slower data rate. An averaging decimator, coupled with the memory, is used for applying to the data a low pass filtering function and the output of the averaging decimator is provided to an infinite impulse response (IIR) filter that receives data from the averaging decimator and provides an output data to a finite impulse response (FIR) filter for applying a band pass function to the data. Lastly, a box car filter interpolates the data received from the FIR filter in a manner which increases the perceived resolution of the data by a given factor, preferably by a factor of 4.

Preferably, the FIR filter is said to provide the frequency selectivity response which provides a 6 dB low pass filter point which is approximately 6% of the filter clock applied thereto. The clock rate can be set at any level and preferably is set in a range of 12.5 MS/s to 100 MS/s (mega-samples per second) or more. The filter may be implemented as a MAC filter.

Other features and advantages of the present invention will become apparent from the following description of the invention which refers to the accompanying drawings.

BRIEF DESCRIPTION OF THE DRAWINGS

FIG. 4 is a block diagram of a tunable digital filter.

FIG. 6b is a waveform and data diagram for the system of FIG. 6a.

FIG. 7b is a waveform and data diagram for the system of FIG. 7a.

FIG. 8b is a waveform and data diagram for the system of FIG. 8a.

FIG. 9b is a waveform and data diagram for the system of FIG. 9a.

DETAILED DESCRIPTION OF PREFERRED EMBODIMENTS OF THE INVENTION

Figure 1:
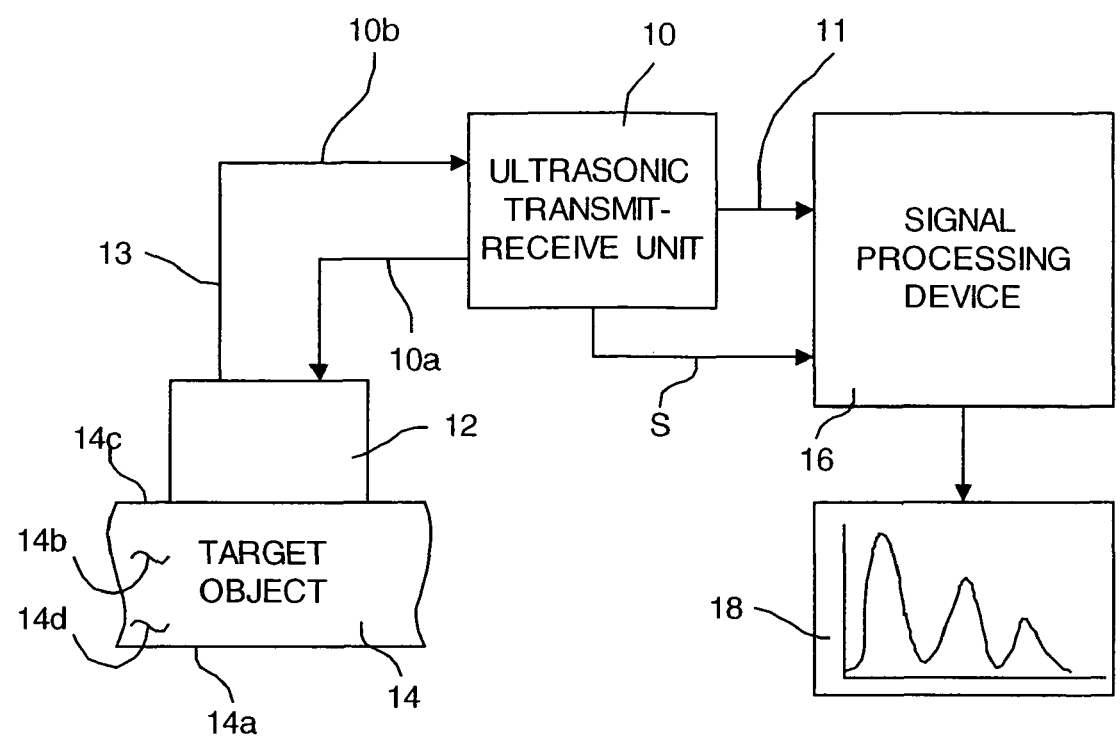
FIG. 1 is block diagram of a basic arrangement of an ultrasonic inspection apparatus.
Figure 2:
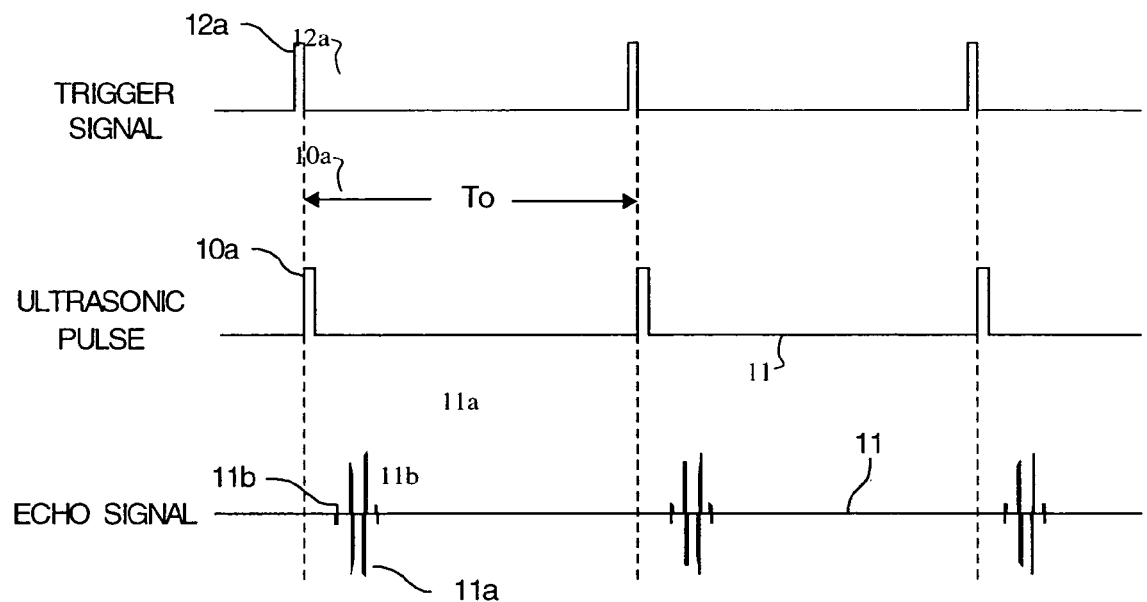
FIG. 2 is a basic waveform diagram for the device of FIG. 1.

Reference is initially made to FIGS. 1 and 2, to provide background information on the general environment of and various problems solved by the present invention.

In FIG. 1, an ultrasonic transmit-receive unit 10 transmits an ultrasonic pulse signal 10a at a predetermined period to a probe or transducer 12 which is coupled to a target object 14, such as to steel material, directly or through a delay material such as water or quartz. As shown in FIG. 2, the probe 12 converts the trigger pulse signal 12a into an ultrasonic pulse 10a which it transmits through the target object 14. The ultrasonic pulse 10a applied into the target object 14 is subsequently reflected by a bottom surface 14a of the target object 14 and received by the probe 12. The probe 12 converts the reflected wave into an electrical signal which is supplied as an electrical echo signal 10b to the ultrasonic transmit-receive unit 10. The ultrasonic transmit-receive unit 10 amplifies the electrical signal 10b and transmits the amplified signal 11 to a signal processing device 16 as an echo signal 11.

The echo signal 11 includes a bottom surface echo 11a corresponding to the wave reflected by the bottom surface 14a and a flaw echo 11b caused by a flaw 14b in the object 14. In addition, the frequency of the ultrasonic echo pulse 11 is determined by the thickness or other property of the ultrasonic vibrator incorporated in the probe 12. The frequency of the ultrasonic pulse 10a used for inspection is set to tens of kHz to tens of MHz. Therefore, the frequency range of the signal waveforms of the bottom surface echo 11a, and the flaw echo 11b included in the echo signal 11 cover a wide range of from 0 Hz to tens of MHz.

The signal processing device 16 performs various signal processing of the echo signal 11 received from the ultrasonic transmit-receive unit 10, and the signal processing device 16 displays on a display unit 18, an output result that represents the presence/absence of a flaw or flaws. In order to signal process the echo signal 11 and display the echo signal, a trigger signal S synchronized with the pulse signal 10a is supplied from the ultrasonic transmit-receive unit 10 to the signal processing device 16.

In the flaw inspection apparatus arranged as described above, the echo signal 11 output from the ultrasonic transmit-receive unit 10 includes, in addition to the bottom surface echo 11a and flaw echo 11b, a certain amount of noise. When the amount of noise included in the ultrasonic pulse 11 is large, the reliability of an inspection result is considerably degraded. The noise is roughly classified into electrical noise and material noise.

The electrical noise comprises external noise caused by mixing an electromagnetic wave into the probe 12, the ultrasonic transmit-receive unit 10, connection cables, e.g., cables 13, or the like, and internal noise generated by amplifier(s) and the like incorporated in the ultrasonic transmit-receive unit 10.

Reduction of the noise included in the echo signal 11 is very important to perform ultrasonic inspection at high accuracy. Conventionally, an analog filter is used to reduce noise components included in the echo signal 11. For example, a BPF (Band pass Filter) is used to pass the frequency component of the ultrasonic echo relative to the electrical noise having a wide-frequency component. In addition, an LPF (Low-Pass Filter) or a BPF is used for material noise, recognizing that the frequency distribution of the flaw echo 11b (FIG. 2) is lower than that of the echo produced by signal scattering. In this manner, when an analog filter is used, noise components included in the echo signal 11b can be reduced to a level equal to or lower than a predetermined level.

It is generally known that the frequency distribution of a flaw echo signal changes based on the ultrasonic attenuation characteristics of the target object 14. Therefore, when a BPF is to be used for material noise represented by a scattered echo or the like, a filter having optimal characteristics is desirably used in accordance with the target object 14. However, since the passing frequency characteristic of the analog filter cannot be easily changed, a larger number of filters, having different passing frequency characteristics corresponding to the different ultrasonic attenuation characteristics of the various materials associated with target objects 14 must be prepared. In this manner, when different filters are used in accordance with the material characteristics of target object 14, practical difficulties occur in consideration of operability or economic advantages versus the cost and complexity of the overall system.

In some cases, the flaw echo 11b may be very close to the front surface 14c of target object 14 which will place it in close proximity to the trailing edge of transmitted pulse 10a. For this reason, it is desirable for the end of the trailing edge (magnified as trailing edge 10at in FIG. 3) of the transmitted pulse 10a to settle to the zero base line 10ab as quickly as possible in order not to interfere with the returning flaw echo 11b. The settling time to the zero base line 7a is a determining factor of a flaw detector's near surface resolution.

Considering that the gain of the ultrasonic transmit-receive unit 10 can be adjusted up to 110 dB (as required by European standard EN 12668-1), a small amount of base line error prior to a gain amplification stage in the ultrasonic transmit-receive unit 10 will cause a large error at the output of the gain amplification stage if the gain level is set too high.

The resulting base line error at the input to the signal processing device 16 will either:

(a) cause the dynamic range to be reduced because the maximum vertical displacement of the signal on the screen will be reduced by the amount of offset of the base line, which produces a reduction in the instrument's sensitivity to detecting flaw echoes, or (b) if sufficiently high in amplitude, cause a gain amplification stage, or gain amplification stages, to saturate, thereby preventing an echo signal from being detected at all.

Conventionally, the base line error problem described above is addressed in one of two ways. In accordance with a first approach, a HPF is used in the signal path of the input of ultrasonic transmit-receive unit 10 in order to filter out the low frequency content of the trailing edge 10at of the transmitted pulse 10a. The trailing edge 10at of the transmitted pulse 10a can be improved by the HPF as is indicated by the approximated dotted line 7c.

However, the effectiveness of the HPF solution is limited in several manners. First, the HPF cutoff frequency (fHPF−3 dB) must be as high as possible to minimize the low frequency content of the trailing edge 10at of the transmitted pulse 10a. For example, if the excitation frequency of probe 12 is 10 MHz and the fHPF−3 dB is 5 MHz, the undesirable effect on the receiver base line is greatly reduced.

Unfortunately, it is not uncommon to use an excitation frequency for probe 12 as low as 500 kHz which would require the fHPF−3 dB to be below 500 kHz. The HPF solution loses much of its effectiveness in this frequency range because an undesirable amount of the low frequency content of the trailing edge 10at of the transmitted pulse 10a is allowed to pass through the HPF and contribute to base line error.

Secondly, the maximum amplitude of the transmitted pulse applied to a first amplifier stage (not shown) of ultrasonic transmit-receive unit 10 is limited (clamped) to a few volts in order to prevent damage to the amplifier circuit. It is common to operate the gain of the ultrasonic transmit-receive unit 10 at a level that will cause the amplifiers to saturate every time the pulser is fired. If the filters are not critically damped, the filter response after coming out of saturation will cause the trailing edge of the transmitted pulse 10a to be worse than if no filtering was applied. It is possible for each manufactured instrument to have the numerous filters tuned to ensure critical damping; however, practical difficulties occur in consideration of manufacturability and long term temperature drift of the filter components.

It should also be noted that once an amplifier goes into saturation, it takes a significant amount of time for the amplifier to return to the linear region of operation. This causes the trailing edge of the transmitted pulse 10a to take more time to return to the zero base line than would be the case if the amplifier input signal remained below the saturation level (i.e. within the linear range of operation).

An alternate method used to address the base line error problem is to directly couple the clamped transmitted pulse 10a to the input of ultrasonic transmit-receive unit 10. This method avoids one of the problems described above, because no HPF or BPF filters are used.

The effectiveness of the direct coupling solution is limited in two ways. First, it does nothing to reduce the low frequency content of the trailing edge 10at of the transmitted pulse 10a. Secondly, the DC component of the base line error and the offset errors of the amplifiers of the ultrasonic transmit-receive unit 10 pass through the signal path and are amplified. This can cause various dynamic range and saturation problems described further on.

Conventionally, flaw detectors have provisions that allow the user to operate the instrument either with filters or through direct coupling in order to select the optimal setting for the flaw measurement scenario.

Figure 3:
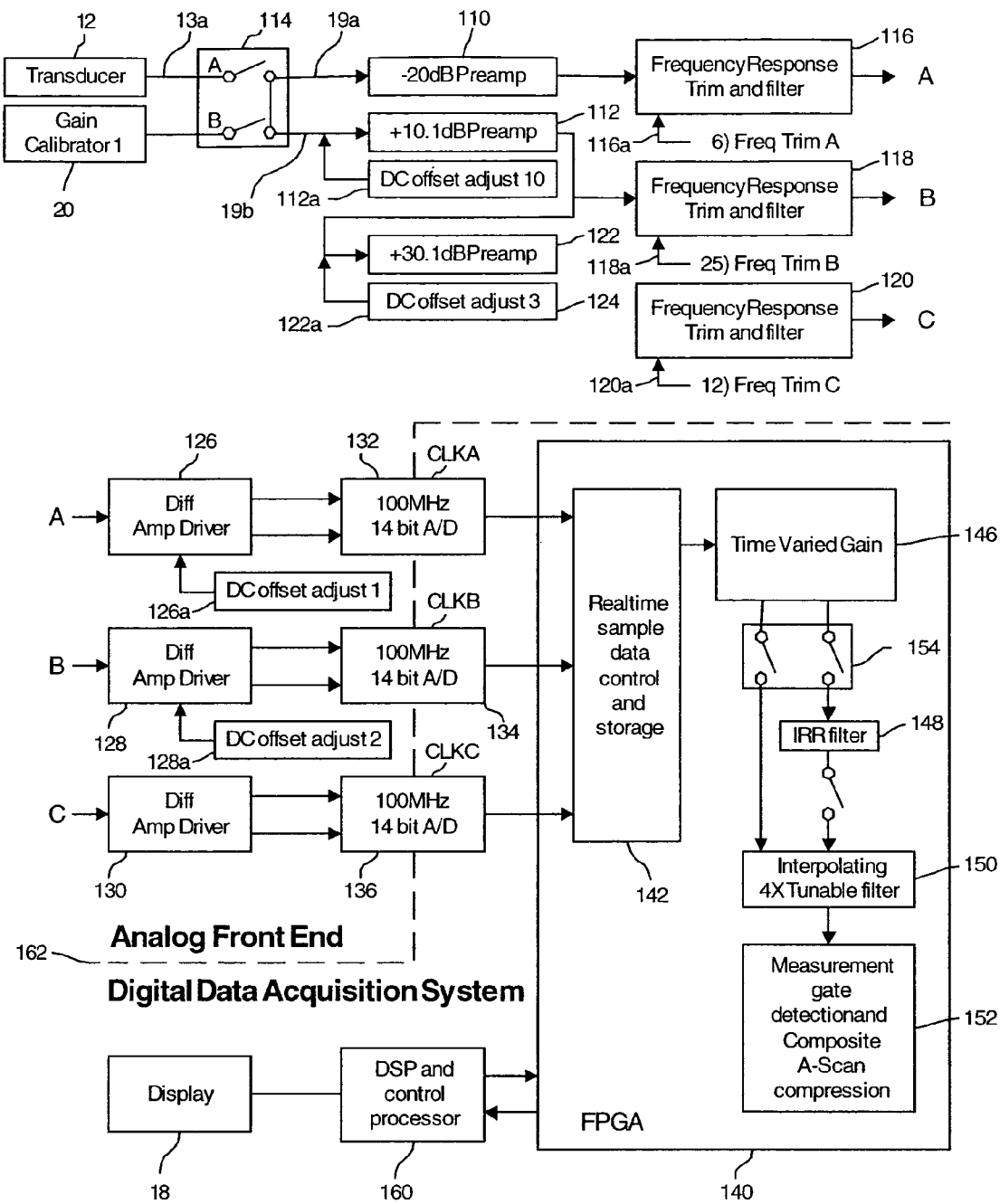
FIG. 3 is an overall circuit diagram of a digitally intensive implementation of an ultrasonic inspection apparatus in accordance with the present invention.

Referring now to FIG. 3, the transducer 12 has its output 13a provided directly to only two preamplifiers 110 and 112, but the latter amplifier feeds a third amplifier 122. The signals of these amplifiers are processed, respectively, in frequency response trim and filter blocks 116, 118 and 120 and subsequently provided along the three channels A, B, C to differential amplifier drivers 126, 128 and 130. The analog signals along the three channels are then provided directly to A/D converters 132, 134 and 136, respectively, whose digital outputs in turn are then supplied to the field programmable gate array 140, which incorporates a control and storage block 142, a digital logarithmic integrator time varied gain 146, and a measurement gate detection and composite A-scan compression circuit 152. This FPGA 140 works in conjunction with the DSP 160, which provides its signal to the display 18.

With reference to the field programmable gate array 140 of FIG. 3, attention is now directed to FIG. 4 which implements a portion thereof, including its real time sample data control and storage, filtering function and interpolating functions.

Preliminarily, it is noted that the block diagram of FIG. 4 effectively provides a tunable digital filter with adaptable sampling rates that are dependent on the pass band settings of the device. The device is intended for use in ultrasonic and eddy current industrial test instruments.

The definition of the terms below applies to the embodiments of the present invention described in this document:

Sample data: The output data produced by an analog to digital converter system

Sample rate: The rate at which sample data was sampled by an analog to digital converter, expressed in MS/s. The sample rate is considered a property of this data and is equivalent to 1/(time period assigned to each sample value).

Effective sample rate: The sample rate of data that is derived from the sample data provided at the output of the analog to digital converter, expressed in MS/s. The effective sample rate is considered a property of the data and is equivalent to 1/(time period assigned to each sample value).

Sampling rate: The rate at which an analog to digital converter samples its input signal, expressed in Million cycles per second (MHz).

Data transfer rate, transfer rate, or data rate: The rate at which data is moved from one stage of the signal processing path to the next, expressed in MHz.

Data processing rate or processing rate: The rate at which data is processed at a specific location within the signal processing path, expressed in MHz.

The interpolator part of the invention creates an effective sample rate of 400 MS/s for frequencies below the Nyquist frequency (50 MHz) while using only 100 MS/s A/D converter sample data.

Existing Flaw Detector products, such as the instant assignee's Epoch 4 Series, have an interleave function that effectively increases the A/D converter sample clock resolution by performing two successive measurement cycles.

An undesirable effect due to interleaving occurs when the transducer probe and object being inspected are in motion relative to one another. To obtain an accurate measurement result during interleaving, the ultrasonic measurement event must be repeatable. Therefore, the placement of the transducer probe with respect to the object being tested must be as unchanged as much as possible during the interleave period.

In a novel manner, the approach of the present invention achieves an effective 4× increase of the sampling rate above the A/D converter sampling rate without the need for multiple measurement cycle interleaving.

With further reference to FIG. 4, the RAW RAM 205 basically corresponds to the element 142 in FIG. 3 and constitutes the device that stores the data from the analog to digital converters, such as the converters 132, 134, 136 of FIG. 3. The RAW RAM 205 can store and playback data, at a data transfer rate of 100 MHz. Operating at clock rate of, for example, 25 MHz, data read from RAW RAM 205 is fed to averaging decimator 206, which receives an enable signal 201 and provides sample or effective sample data, depending on whether averaging decimator 206 is disabled or enabled, respectively, to an IIR (Infinite Impulse Response) filter 207 which filters the data based on a filtering function defined by operator settable values stored in IIR coefficient registers 202. As shown in FIG. 4b, it is within the purview of the invention that averaging decimator 206 precede RAW RAM 205, and RAW RAM 205 provide its output to IIR filter 207. This infinite impulse response type filter operates at a rate which is determined by a filter clock 212 which is enabled by a filter clock enable 211 and provides the gated filter clock 216 to the IIR filter 207, as shown.

A finite impulse response (FIR) filter 208 provides a further filtering function that is shaped and defined by data stored in FIR coefficient registers 203. The FIR filter 208 operates synchronously with the IIR filter 207. A box car filter 209 receives sample data from the FIR filter 208 and provides its data output in the form of data 215. The box car filter 209 operates at the rate of the filter clock 212 and is further controlled by a box car depth signal 213 as shown.

Thus, the circuit of FIG. 4 filters digital data while providing optimal filter response and while requiring minimal digital hardware in the form of logic gates, gate arrays, and the like. The minimization of the digital hardware reduces the size and cost required for the FPGA (field programmable gate array), and provides power consumption reductions. Low power consumption is important for achieving a longer battery life in portable instruments. Further, the invention also reduces part count considerably and improves pass band frequency control as compared to the analog filter implementation.

The invention includes provisions for:

a) 'playing back' sample data 204 (DATA_IN) from the RAW RAM 205 at one fourth the 100 MS/s A/D converter sampling rate, resulting in a data transfer rate from RAW RAM 205 of 25 MHz.

b) interpolating data entering the Box Car Filter 209 to maintain a constant 400 MS/s effective sample rate.

The interpolator contained within the invention allows the use of lower frequency filter clock 212 (100 MHz) than would be required by conventional digital filter implementations. The use of a lower frequency filter clock also reduces power consumption because power consumption is directly proportional to clock speed.

In accordance with one aspect of the invention, the optimal frequency selectivity response for FIR low pass filter 208 is achieved when the relationship between the −6 dB frequency (fLPF−6 dB) and filter clock frequency 12 (FILTER_CLK) is:

$$f_{LPF-6dB} < 10\% \text{ of FILTER\_CLK} \qquad \text{[EQUATION1]}$$

The relationship expressed in EQUATION 1 is based on the topology of the FIR filter used in the described embodiment of the invention which is a symmetrical 32 tap MAC filter with 32 coefficients. This is a desirable topology because it provides very good frequency selectivity response with only sixteen digital hardware multipliers and moderate memory capacity. Only sixteen digital hardware multipliers are required for the 32 coefficients because each of the 16 values is used twice in a symmetric FIR filter.

As described above, the digital output signal of a 100 MS/s A/D converter such as of any of the converters 132, 134, 136 (FIG. 3) is connected to a digital logic circuit (not shown) that transfers DATA IN 204 to RAW RAM 205 at a rate of 100 MHz. The continuous transfer of sample data from RAW RAM 205 to Averaging Decimator 206 is synchronously controlled by CLK 25M 210, at a 25 MHz processing rate. It is important to note that the 100 MS/s A/D converter runs in a burst mode for only a fraction of each measurement period (e.g. 200µ seconds out of 1 ms). Therefore, the post processing apparatus has sufficient time to process all the data continuously with no data buffer overflows.

Figure 5:
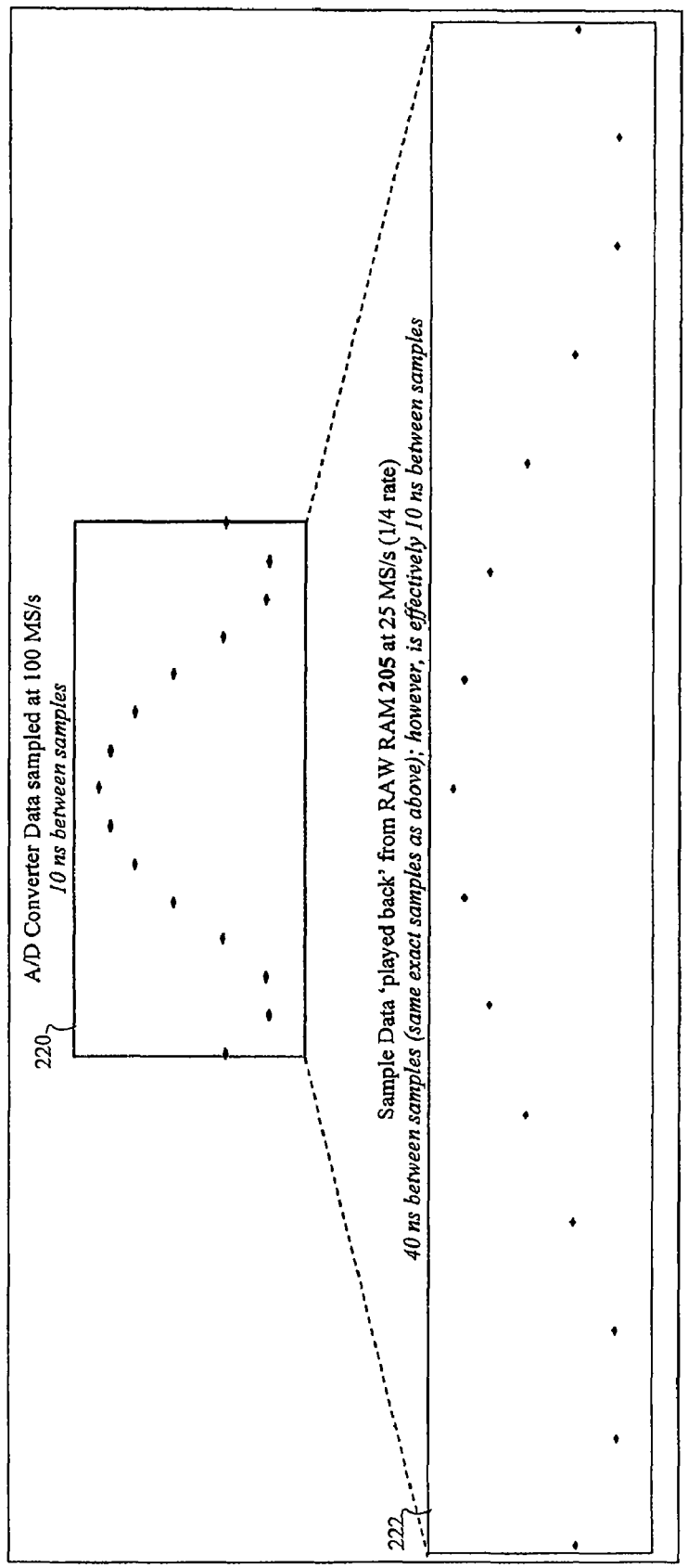
FIG. 5 is an illustration that compares sampled data rate to playback data rate in the context of the present invention.

FIG. 5 illustrates the effective difference in time scale between the 100 MS/s sample data 220 and the same data 222 played back from RAW RAM 205 at a 25 MHz data transfer rate. The sample data shown in FIG. 5 as data points 220 and 222 are identical except for the rate at which they are processed.

This data play back concept sets the foundation for the use of a variable Filter Rate clock to maintain as close as possible the relationship expressed in the aforementioned EQUATION 1 (repeated below for convenience)

$$f_{LPF-6dB} < 10\% \text{ of FILTER\_CLK} \qquad \text{[EQUATION1]}.$$

This concept achieves a 400 MS/s effective sample resolution with only 100 MS/s A/D converter sample data and 100 MHz maximum data processing rate.

Implementation details of IIR Filter 207 and FIR Filter 208 are described below.

As is known, a second order IIR filter works with the following equation:

$$D_{out}[n] = (D_{in}[n]*A0) + (D_{in}[n-1]*A1) + (D_{in}[n-2]*A2) + (D_{out}[n-1]*B1) + (D_{out}[n-2]*B2)$$

With A0, A1, A2, B1, and B2 representing the filter coefficients.

These five coefficient values are calculated by software and loaded into the registers to tune the IIR filter 207 to create a variable frequency, 2nd order high pass filter. In this way, the IIR filter will be tunable to allow the end user to build (in concert with the FIR filter section) an extremely divergent range of filter characteristics required for various applications.

The following formula should be used to generate the five IIR filter coefficients:

$$c = sqrt(3)*(sqrt(2-0.75)-0.5);$$

$$Fc = 0.5 - (c*Fo/Fs);$$

$$wo = \tan(\pi*Fc);$$

$$K1 = 3*wo;$$

$$K2 = 3*(wo)^2;$$

$$A0 = K2/(1+K1+K2);$$

$$A1 = -(2*A0);$$

$$A2 = A0;$$

$$B1 = -(2*A0*(1/K2-1));$$

$$B2 = 1 - (A0+A1+A2+B1);$$

where,
 c=3 dB cutoff correction factor
 Fo=desired −3 dB cutoff frequency
 Fc="corrected" −3 dB cutoff frequency
 A0, A1, A2, B1, B2=IIR filter coefficients As is further known, a FIR works by digitally convolving the input data with the 32 filter coefficients (each of the 16 input values is used twice in a symmetric FIR). The 16 filter coefficient values are calculated and loaded into registers by software to specify the −6 dB roll off point(s) of the low (band) pass filter. In this way, the FIR filter will be tunable to allow the end user to build (in concert with the IIR filter section) an extremely divergent range of filter characteristics required for various applications.

Depending on the sixteen coefficient values loaded, the FIR filter can function as a band pass or low pass filter. The calculations for these coefficients are listed below.

To put the FIR in low pass mode, the following formula should be used to generate the coefficients:

$$n = -((32-1)/2):1:((32-1)/2);$$

$$filter\_imp\_resp[n] = \sin(2*\pi*F_c/F_s*n)/(\pi*n);$$

$$coef[n] = filter\_imp\_resp*win;$$

$$coef = coef/sum(coef);$$

where,
 $F_c$=desired −6 dB Frequency in MHz
 $F_s$=Filter sampling frequency in MHz
 win=hamming window coefficients To put the FIR into band pass mode, the following formula should be used to generate the coefficients:

$$n = -((32-1)/2):1:((32-1)/2)$$

$$filter\_imp\_resp = (2*\sin(\pi*((F_H-F_L)/F_s)*n).*\cos(\pi*((F_H+F_L)/F_S)*n))./(\pi*n)$$

$$coef = filter\_imp\_resp.*win$$

$$f_0 = ((F_H+F_L)/2)/(F_s/2)$$

$$coef = coef/abs(exp(-j*2*\pi*(0:taps-1)*(f_0/2))*(coef.'))$$

where,
 $F_H$=desired high limit cutoff (−6 dB) frequency in MHz
 $F_L$=desired low limit cutoff (−6 dB) frequency in MHz
 $F_s$=Filter sampling frequency in MHz
 win=hamming window coefficients For both cases (band pass and low pass) the hamming window coefficients defined by:
 win[0]=0.08 win[1]=0.089416 win[2]=0.11728
 win[3]=0.16245 win[4]=0.22308 win[5]=0.29668
 win[6]=0.38024 win[7]=0.47034 win[8]=0.5633
 win[9]=0.6553 win[10]=0.74258 win[11]=0.82157
 win[12]=0.88903 win[13]=0.9422 win[14]=0.9789
 win[15]=0.99764 win[16]=0.99764 win[17]=0.9789
 win[18]=0.9422 win[19]=0.88903 win[20]=0.82157
 win[21]=0.74258 win[22]=0.6553 win[23]=0.5633
 win[24]=0.47034 win[25]=0.38024 win[26]=0.29668
 win[27]=0.22308 win[28]=0.16245 win[29]=0.11728
 win[30]=0.089416 win[31]=0.08

In a novel manner, the method of the invention processes the data before it enters Filter 207, adjusts the filter rate via FILTER CLK 212, and deploys novel processing of the data in Box Car Filter 209 after it leaves the FIR filter 208.

The box car filter 209 is simply a device that produces a rolling average of variable depth on the data. Its purpose is to up-sample (through straight line implementation) the data coming out of the FIR and IIR filter stages to provide an output sample rate of 400 MS/sec, regardless of the filter rate.

| Depth | Equation | Sample Frequency Delta |
|---|---|---|
| 1 | data[n] = data[n] | ×1 |
| 2 | data[n] = (data[n] + data[n − 1]/2] | ×2 |
| 4 | data[n] = (data[n] + data[n − 1] . . . + data[n-3])/4 | ×4 |
| 8 | data[n] = (data[n] + data[n − 1] . . . + data[n-7])/8 | ×8 |

The appropriate depth will be selected to maintain an output sample rate of 400 Ms/s regardless of the sample frequency used for the FIR and IIR filters. This will allow a constant interpolation rate of 4:1 while still providing the greatest range of possible cutoff frequencies.

The decimator 206 will only be enabled when a filter rate of 12.5 MHz is selected. When DEC_IN 201 is enabled, every pair of data points will be averaged together and held for both read cycles. The FIR and IIR filters 207 and 208, operating at a rate of 12.5 MS/s, will then read every other data point, effectively reducing the sample rate of the data by two. This method allows for improved preservation of the original signal compared to traditional decimation.

The following describes the behavior of the Two Point Averaging Decimator 206:

When DEC_IN 201 is enabled:
 data[0]=data[1]=(data [0]+data[1])/2
 data[2]=data[3]=(data [2]+data[3])/2
 data[4]=data[5]=(data [4]+data[5])/2
 and so on . . .

When DEC_IN 1 is disabled:
 Data[n]=data[n]

Referring to FIGS. 6a through 9b, for simplicity, all waveforms shown in the various figures are in the pass-band of the filters. Therefore, no out-of-band frequencies are shown in the waveforms.

The following are descriptions of how the invention operates at each filter processing rate setting. For all filter rate settings, the data transfer rate from RAW RAM 205 to Averaging Decimator 206 is 25 MHz. The BOX CAR filter 209 output data rate is 100 MHz. These rates do not change as the filter rate 216 is changed. The oversampled 400 MS/S output data_out 215 from BOX CAR filter 209 is an effective sample rate because it is derived from the 100 MS sample data provided from the analog to digital converter. The present inventor recognizes that the ratio between the A/D Converter sampling rate and the output data transfer rate of RAW RAM 205 may be other than 4:1 in order to realize the preferred embodiment with different filter performance parameters.

In FIGS. 6a, 7a, 8a and 9a, waveforms are shown with sample points that line up vertically in order to clearly show the data processing effect at each stage of the signal processing chain. The preferred embodiment of the invention would actually have one to several 100 MHz clock delays between subsequent waveforms, thereby causing the waveform sample points to be shifted to the right (not shown) as the sample data passes through the signal processing chain.

In FIGS. 6b, 7b, 8b and 9b, processing delays between successive digital signals are shown on the timing diagrams. However, the magnitude of the delays may not match the actual delays of the preferred embodiment of the invention.

FIGS. 6a to 9b present four scenarios (a) to (d) described below.

(a) Effective 400 MS/s Sample Rate with Filter Rate 216 Set to 100 MHz

Figure 6A:
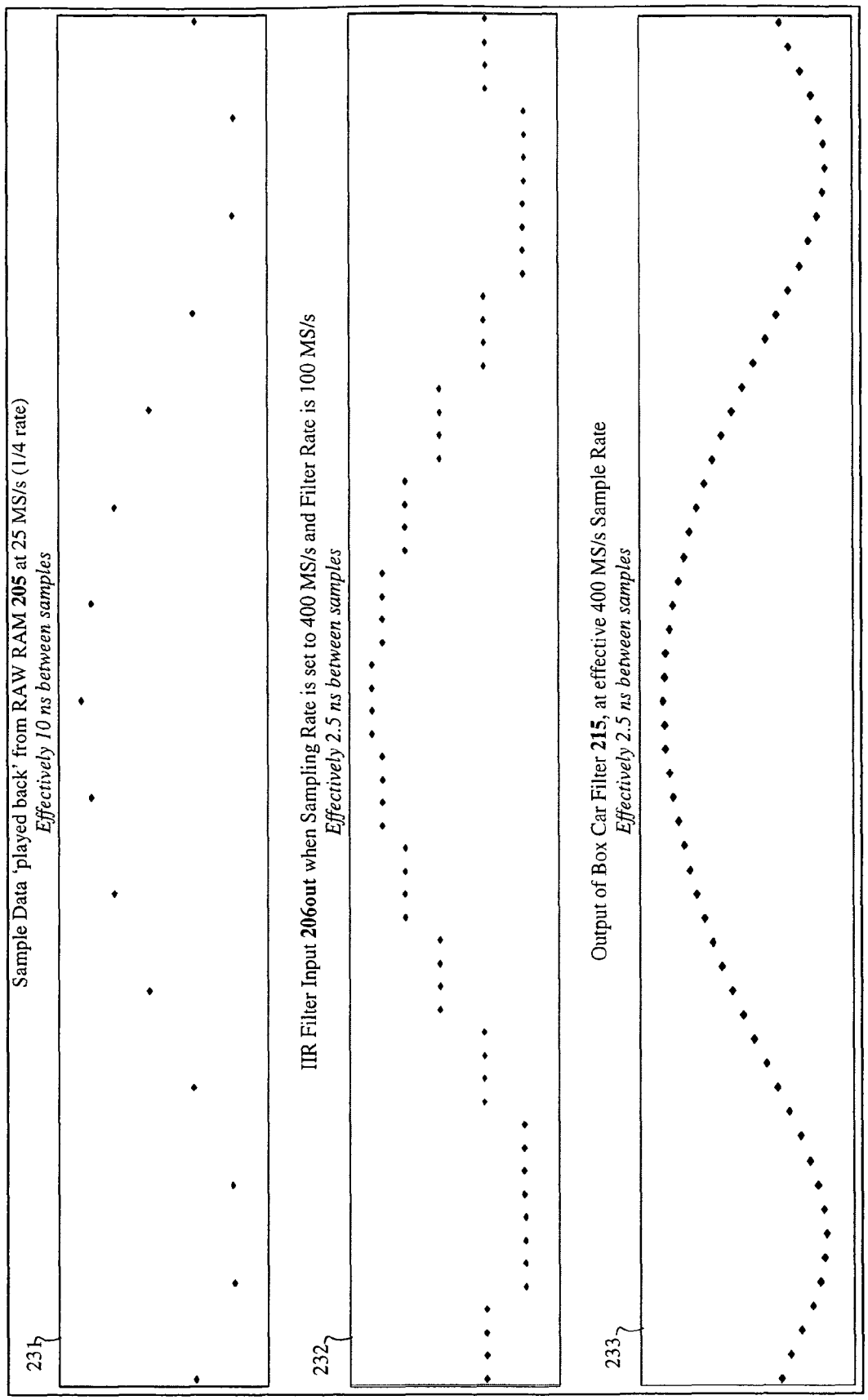
FIG. 6a compares waveforms obtained at different points in the circuit of FIG. 4 for a 100 MS/s filter rate.
Figure 6B:
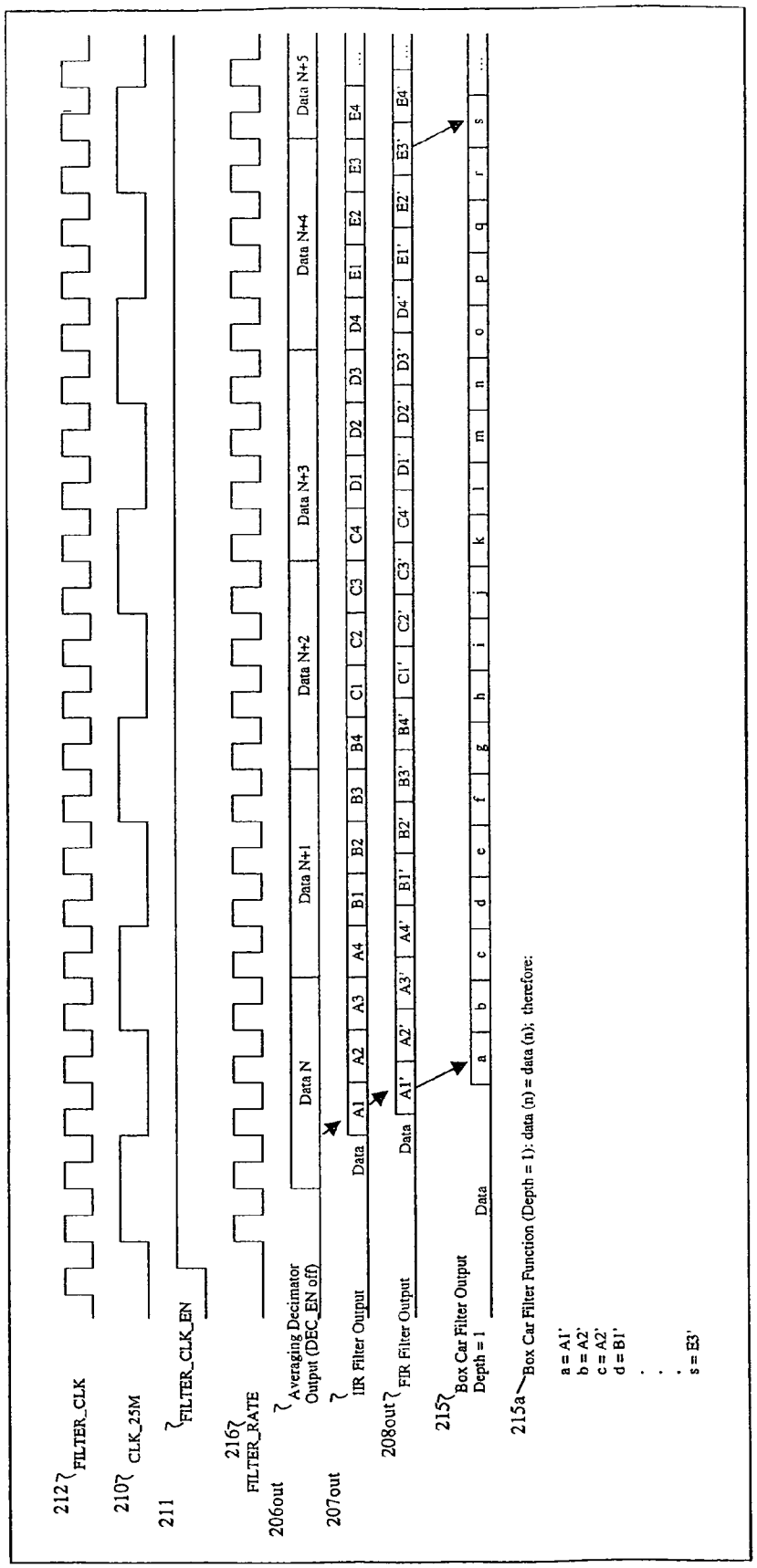

As can be seen from FIGS. 6a and 6b, the output register of Averaging Decimator 206 is updated at a rate of 25 MHz. When Filter_Rate 216 is set to 100 MHz, IIR Filter 207 reads the data from the output register of Averaging Decimator 206 four times for every 25 MHz cycle. Therefore, the same A/D converter data point is read four times resulting in signals 232 and 206out in FIGS. 6a and 6b respectively. This causes the sample data entering IIR Filter 207 to have an effective sample rate of 400 MS/s. The 'stair step' shape of the waveform 232 shown in FIG. 6a is smoothed when it passes through FIR Filter 208 resulting in DATA OUT output 215. The output of FIR Filter 208 is passed through Box Car Filter 209 unchanged because BOX CAR_DEPTH 213 is set to 1 (refer to FIG. 6b, equation 215a for the Box Car).

b) Effective 200 MS/s Sampling Rate with Filter Rate 216 Set to 50 MHz

Figure 7A:
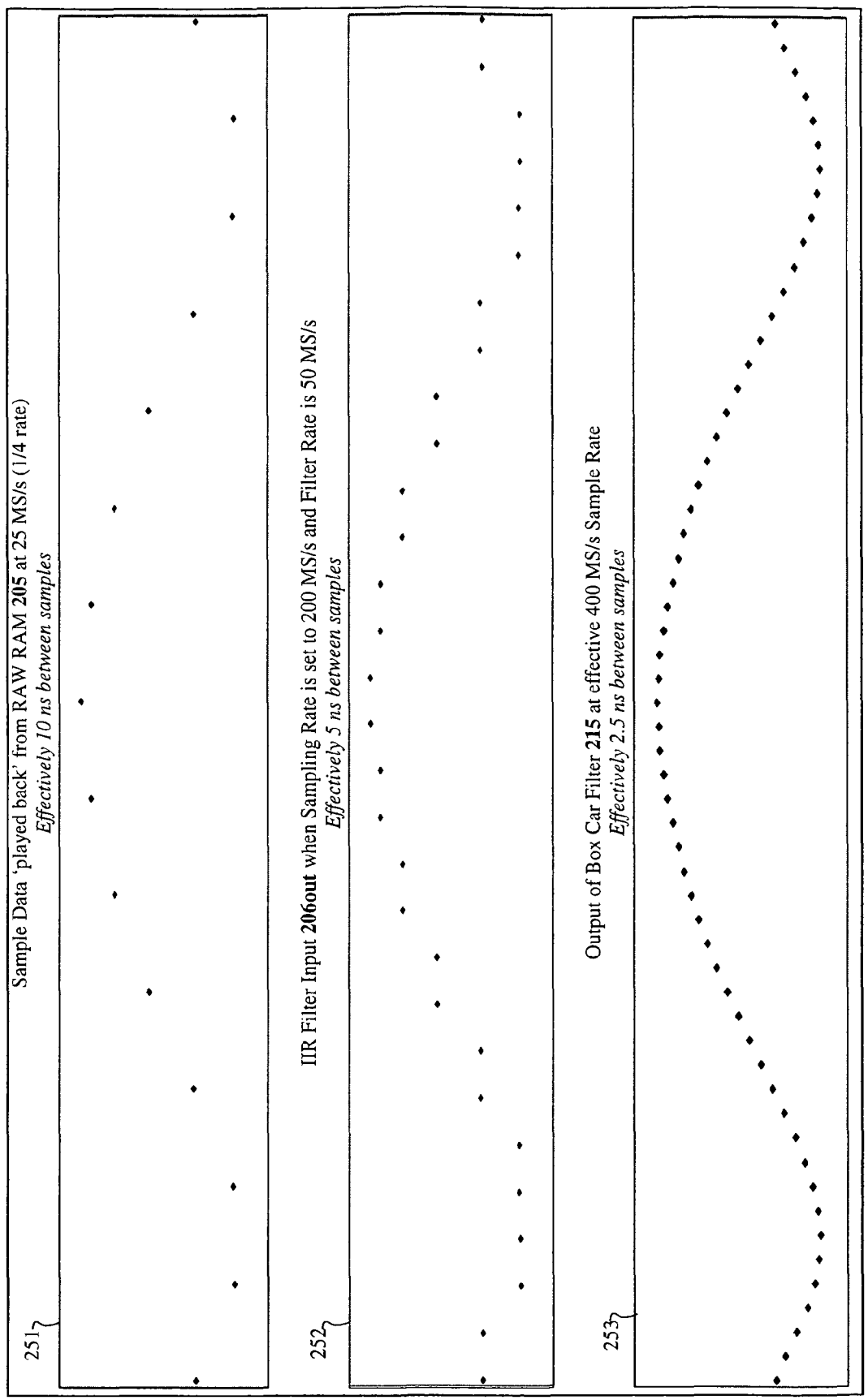
FIG. 7a compares waveforms obtained at different points in the circuit of FIG. 4 for a 50 MS/s filter rate.
Figure 7B:
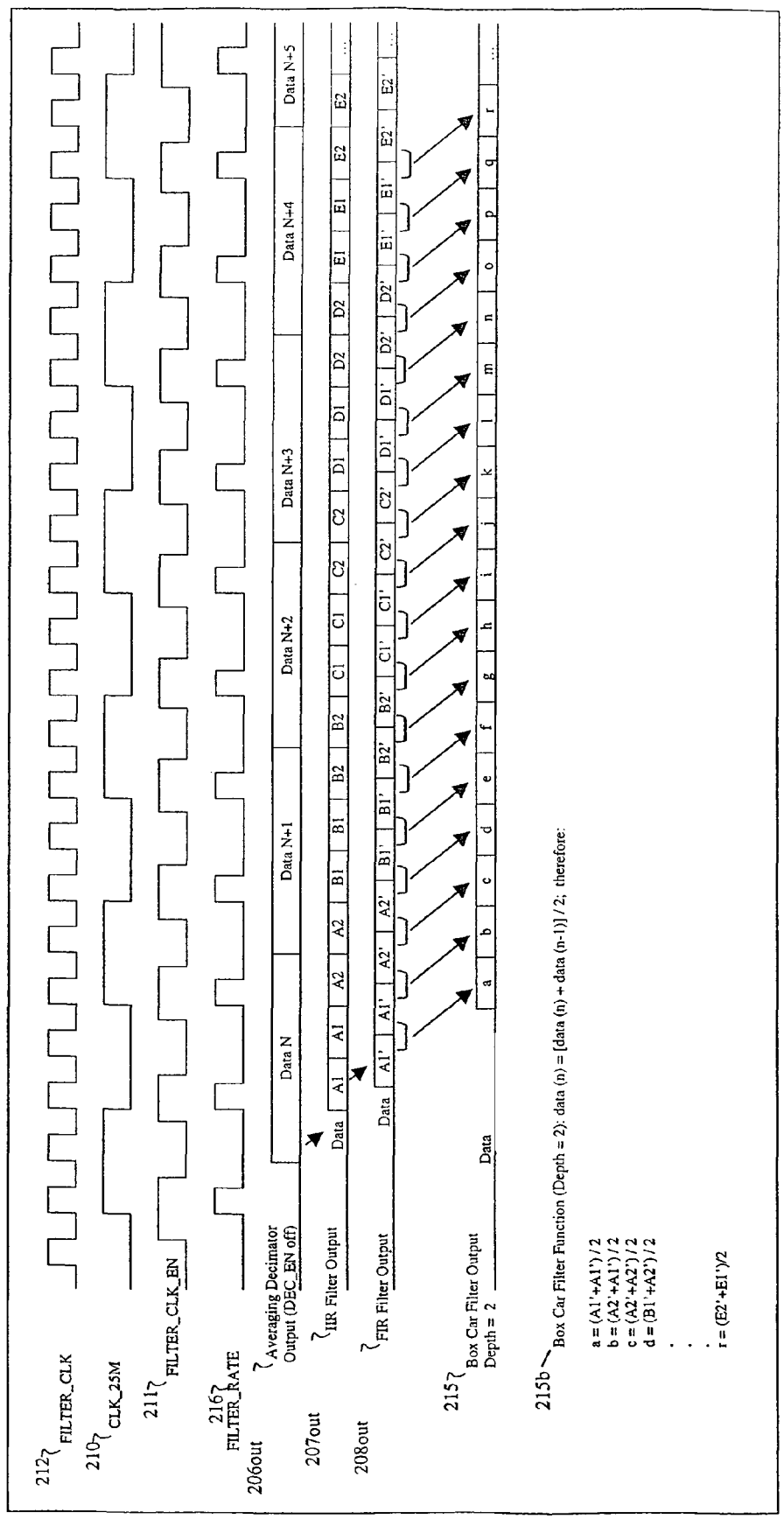

As can be seen from waveform 251 of FIG. 7a and waveform 206out of FIG. 7b, the output register of Averaging Decimator 206 is updated at a rate of 25 MHz. When Filter Rate 216 is set to 50 MHz, IIR Filter 207 reads the data from the output register of Averaging Decimator 206 two times for every 25 MHz cycle. Therefore, the same A/D converter data point is read two times resulting in FIG. 7a, waveform 252 and FIG. 7b waveform 206out. This causes the sample data entering IIR Filter 207 to have an effective sample rate of 200 MS/s. The 'stair step' shape of the waveform shown in FIG. 7a waveform 252 is smoothed when it passes through FIR Filter 208. The output of FIR Filter 208 is then passed through Box Car Filter 209 to increase the effective sample rate of DATA_OUT 215 to 400 MS/s. The BOX CAR_DEPTH signal 213 is set to 2 (as shown in FIG. 7b, equation 215b).

c) Effective 100 MS/s Sampling Rate with Filter Rate 216 Set to 25 MHz

Figure 8A:
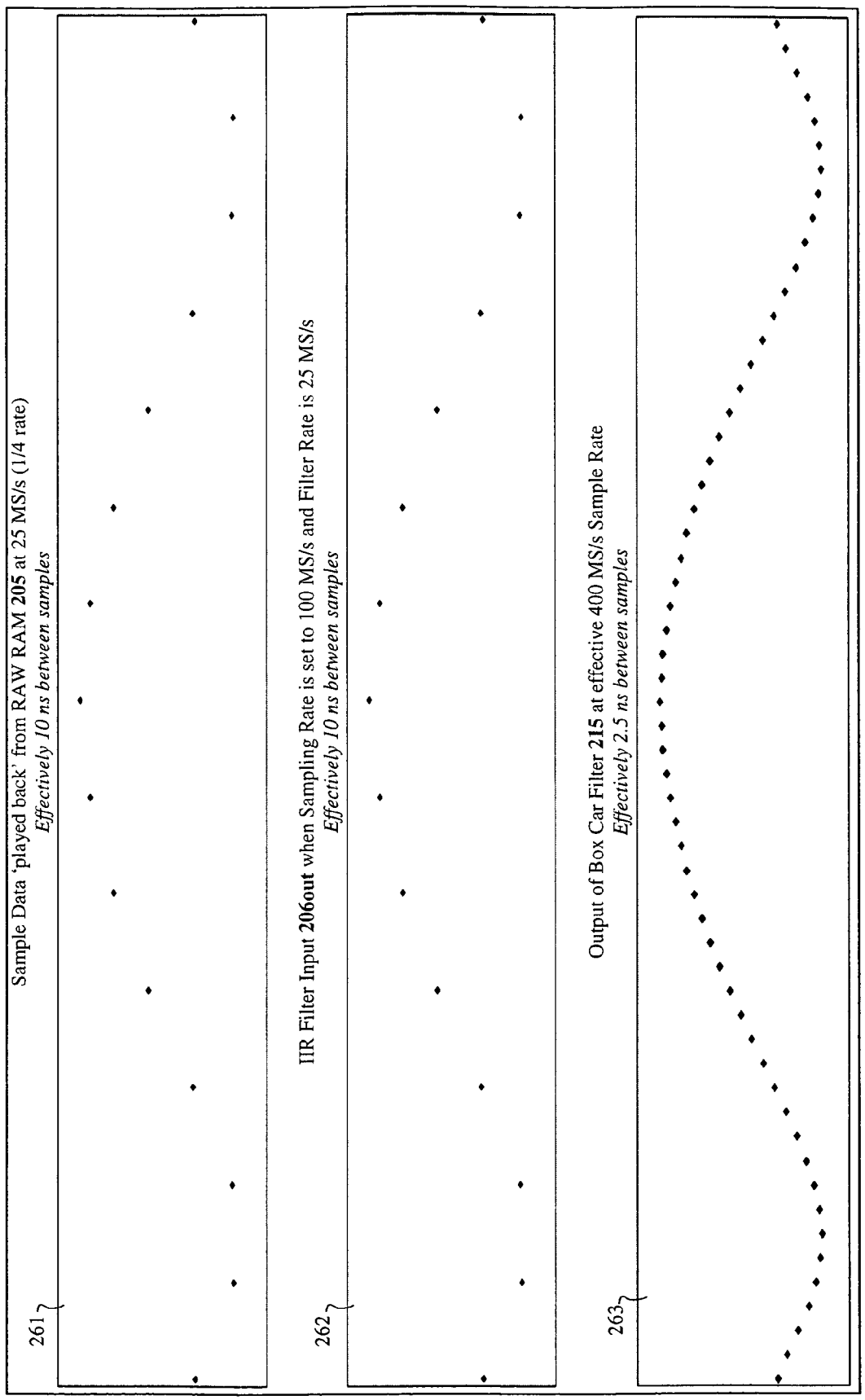
FIG. 8a compares waveforms obtained at different points in the circuit of FIG. 4 for a 25 MS/s filter rate.
Figure 8B:
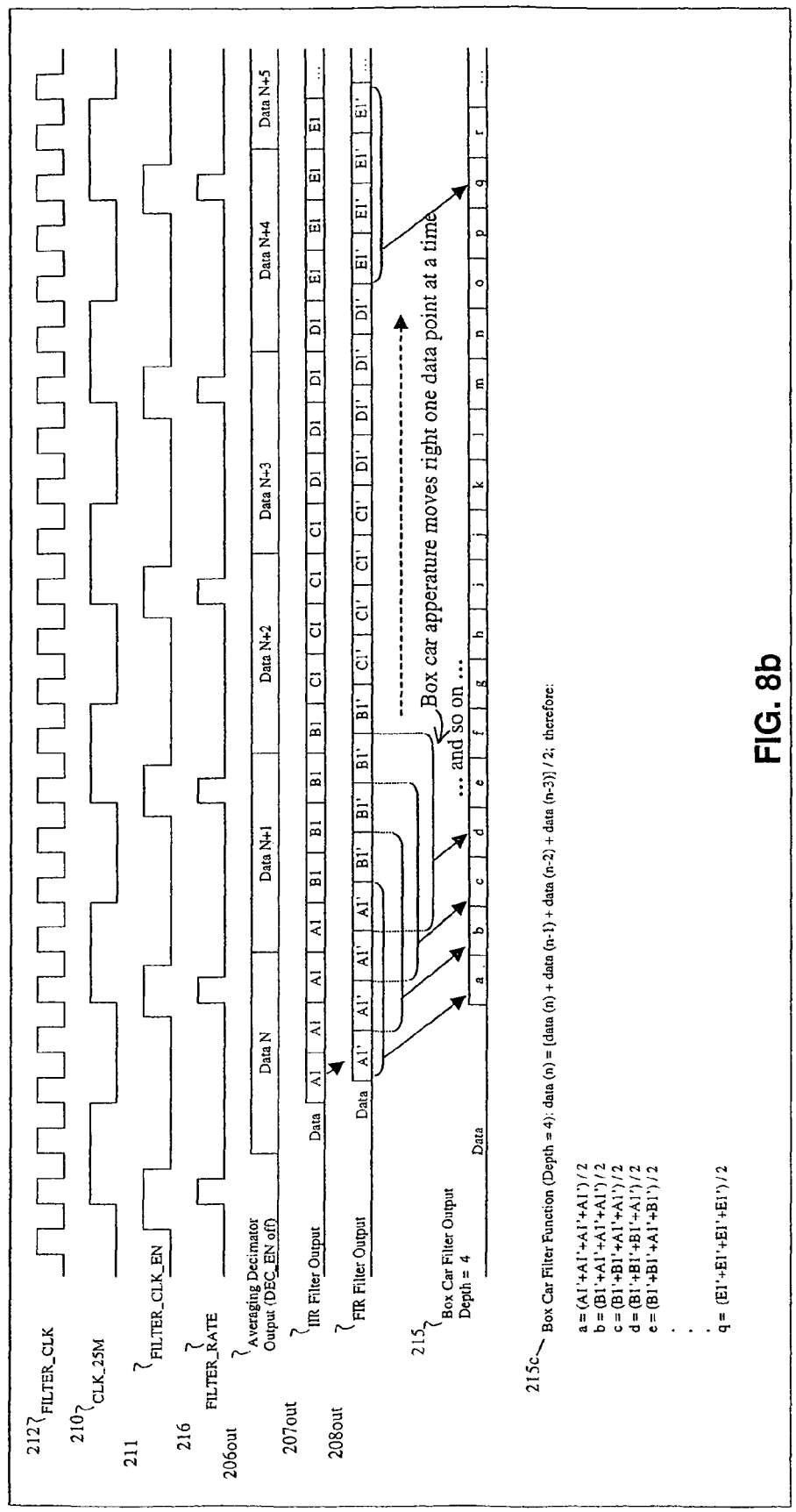

As can be seen from FIG. 8a waveform 261 and FIG. 8b waveform 206out, the output register of Averaging Decimator 206 is updated at a rate of 25 MHz. When Filter Rate 216 is set to 25 MHz, IIR Filter 207 reads the data from the output register of Averaging Decimator 206 once every 25 MHz cycle. Therefore, the same A/D converter data point is read once resulting in FIG. 8a waveform 262 and FIG. 8b waveform 206out. This causes the sample data entering IIR Filter 207 to have an effective sample rate of 100 MS/s as can be seen in FIG. 8a waveform 262. The output of FIR Filter 208 is then passed through Box Car Filter 209 to increase the effective sample rate of DATA_OUT 215 to 400 MS/s as can be seen from waveform 263 of FIG. 8a. The BOX CAR_DEPTH 213 is set to 4 (refer to FIG. 8b, equation 215c for the Box Car).

d) Effective 50 MS/s Sampling Rate with Filter Rate 216 Set to 12.5 MHz

Figure 9A:
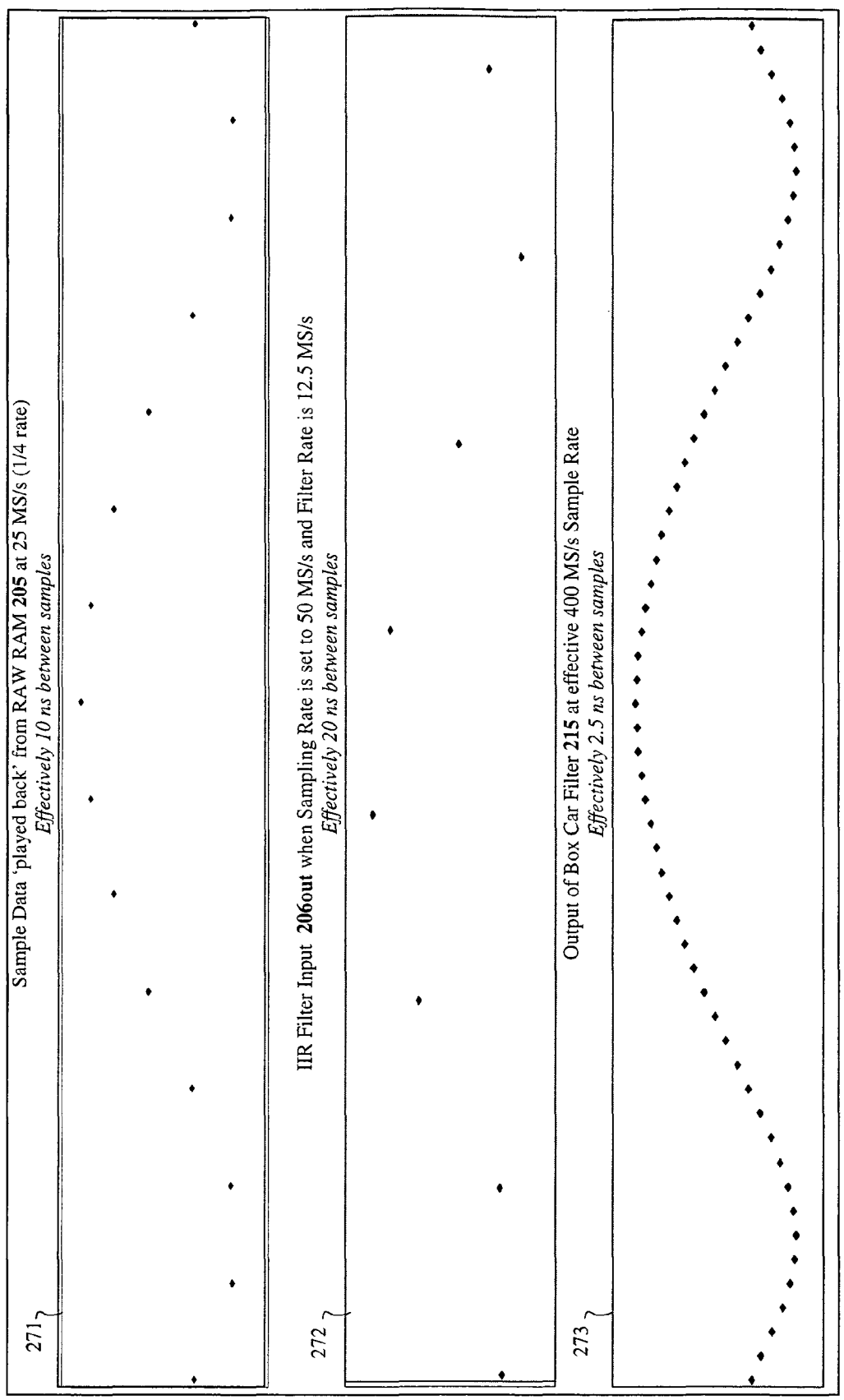
FIG. 9a compares waveforms obtained at different points in the circuit of FIG. 4 for a 12.5 MS/s filter rate.
Figure 9B:
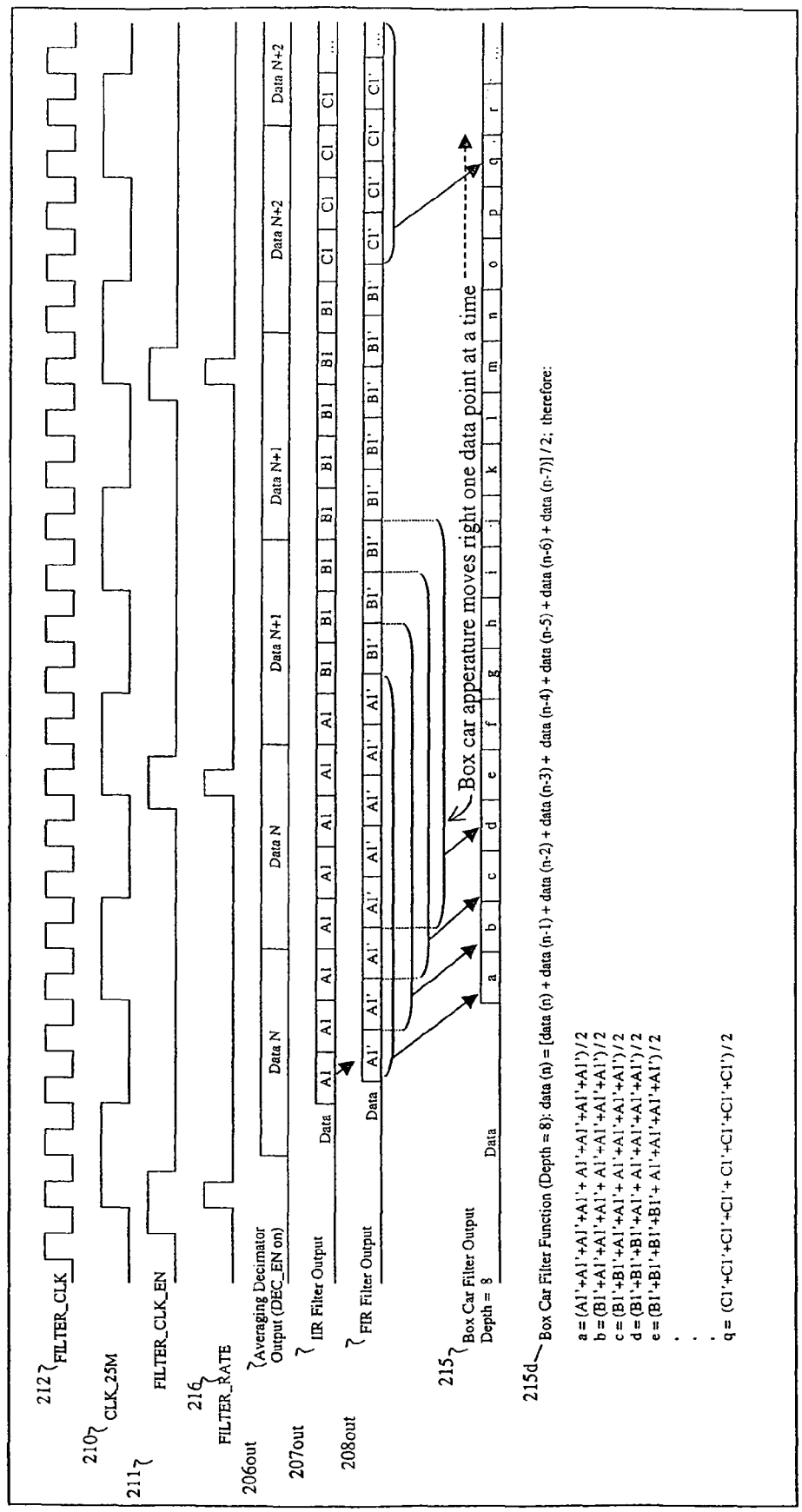

As can be seen from FIGS. 9a and 9b, the output register of Averaging Decimator 206 is updated at a rate of 25 MHz. The DEC_IN signal 201 enables Averaging Decimator 206 to average every pair of data points coming from RAW RAM 205 and holds the results in the output register for two read cycles. When Filter_Rate 216 is set to 12.5 MHz, IIR Filter 207 reads the data from the output register of Averaging Decimator 206 once every other 25 MHz cycle. Therefore, the average of every other A/D converter data point is read once resulting in FIG. 9a waveform 272 and FIG. 9b waveform 206out. This causes the sample data entering IIR Filter 207 to have a sample rate of 50 MS/s as can be seen from FIG. 9a waveform 272. The output of FIR Filter 208 is then passed through Box Car Filter 209 to increase the effective sample rate of DATA_OUT 215 to 400 MS/s as can be seen from waveform 273 of FIG. 9a. The BOX CAR_DEPTH 213 is set to 8 (as shown in FIG. 9b, equation 215d for the Box Car).

An alternate embodiment that achieves the aforementioned benefits of the present invention is described below by reference to the block diagram shown in FIG. 10. The key differences between the present and the alternate embodiment are:

a) the alternate embodiment can change the effective sample rate over a much wider range with very fine resolution as compared to the prior embodiment that uses a decimating method that divides the 100 MS/sec sample data by binary divisors.

b) the alternate embodiment does not change the filter rate to control the IIR and FIR frequency response. Instead, the IIR and FIR filter rate is controlled by Flow Control Logic 322 that moves the data through the data path as needed, the FIR frequency response being controlled by the changing the effective sample rate of the data entering the FIR filter and the coefficients of the IIR and FIR filters.

c) the alternate embodiment includes a second rate adjuster 321 that takes the output of the FIR filter 320 and adjusts the data rate to provide only the data required to generate various display modes, such as rectification and gates, and fill the selected display range.

Figure 10:
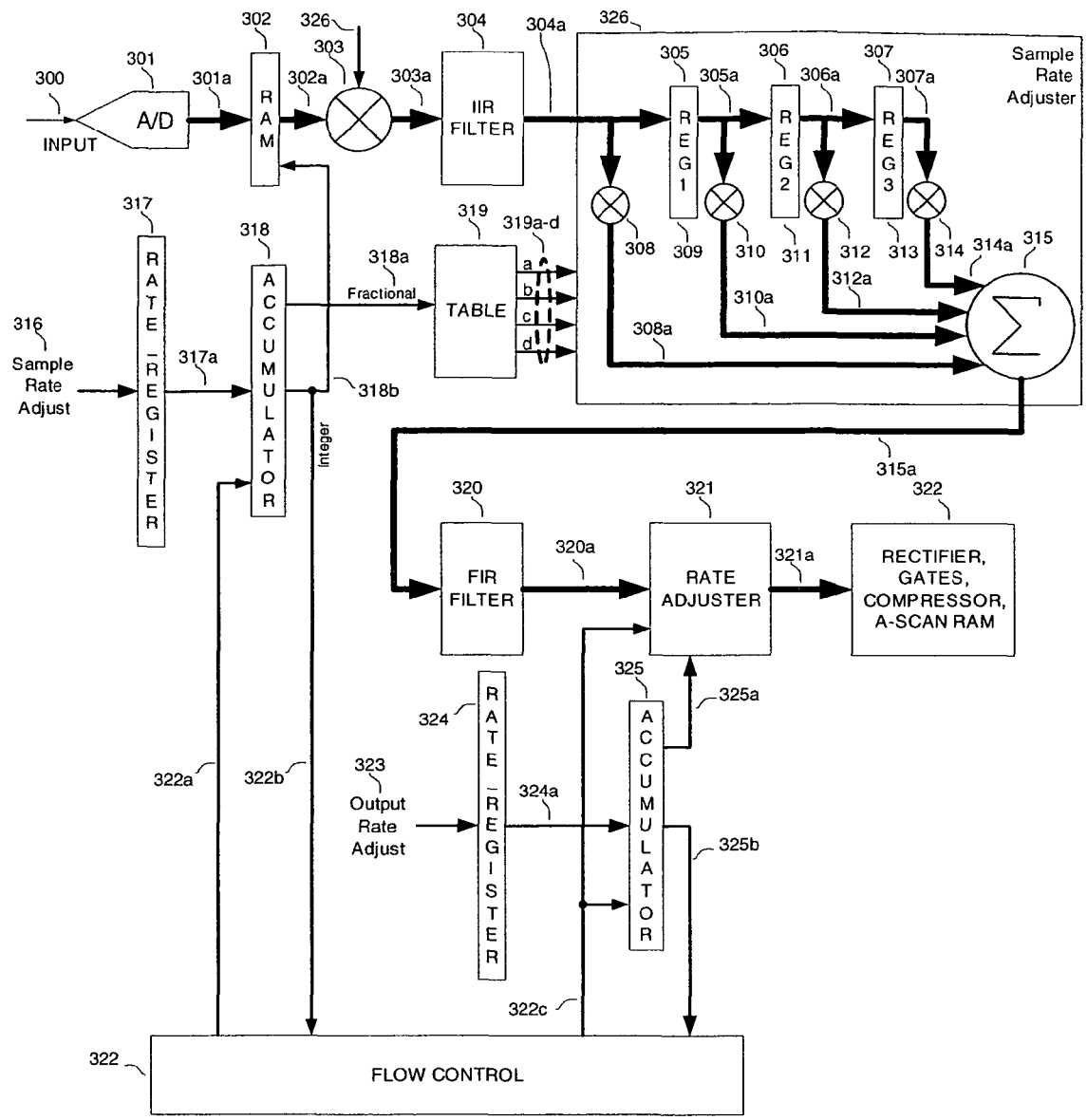
FIG. 10 is a block diagram of another embodiment of a tunable digital filter.

With further reference to FIG. 10, the RAM 302 basically corresponds to the element 142 in FIG. 3 and constitutes the device that stores the sample data from the analog to digital converters, such as the converters 132, 134, 136 of FIG. 3. For simplicity, analog to digital converter 301 in FIG. 10 represents converters 132, 134 and 136 of FIG. 3, or any other converter, not shown. The RAM 302 can store and playback data, at data transfer rates of 100 MHz. Continuing with FIG. 10, Multiplier 303 is used to scale the data provided by output 301a of analog to digital converter 301 to match the sample amplitude resolution required at input 303a of IIR Filter 304 which filters the sample data based on a filtering function defined by operator settable values stored in IIR coefficient registers, not shown. This infinite impulse response, IIR, type filter 304 operates at the same rate as the data transfer rate from RAM 302 which is determined by Flow Control Logic 322.

A novel aspect of the alternate embodiment is Sample Rate Adjuster 326 that creates an effective sample rate depending on the setting of a parameter identified as Output Rate Adjust 323 that is loaded into Rate Register 324. The sample rate created by Sample Rate Adjuster 326 will be referred to as the 'effective' sample rate to distinguish it from the 'actual' sample rate of analog to digital converter 301. Sample Rate Adjuster 326 effectively resamples the actual input sample data to create effective sample data with time values that fall between data points of the input stream. By computing new data that have a different time interval than the input data stream, a new data rate is created—i.e. the effective sample rate. The resampled data rate is adjusted by a ratio that is variable over a wide range with very fine effective sample rate resolution. By changing the sample rate, the total number of points in the output data stream of Sample Rate Adjuster 326 is also adjusted.

Figure 11:
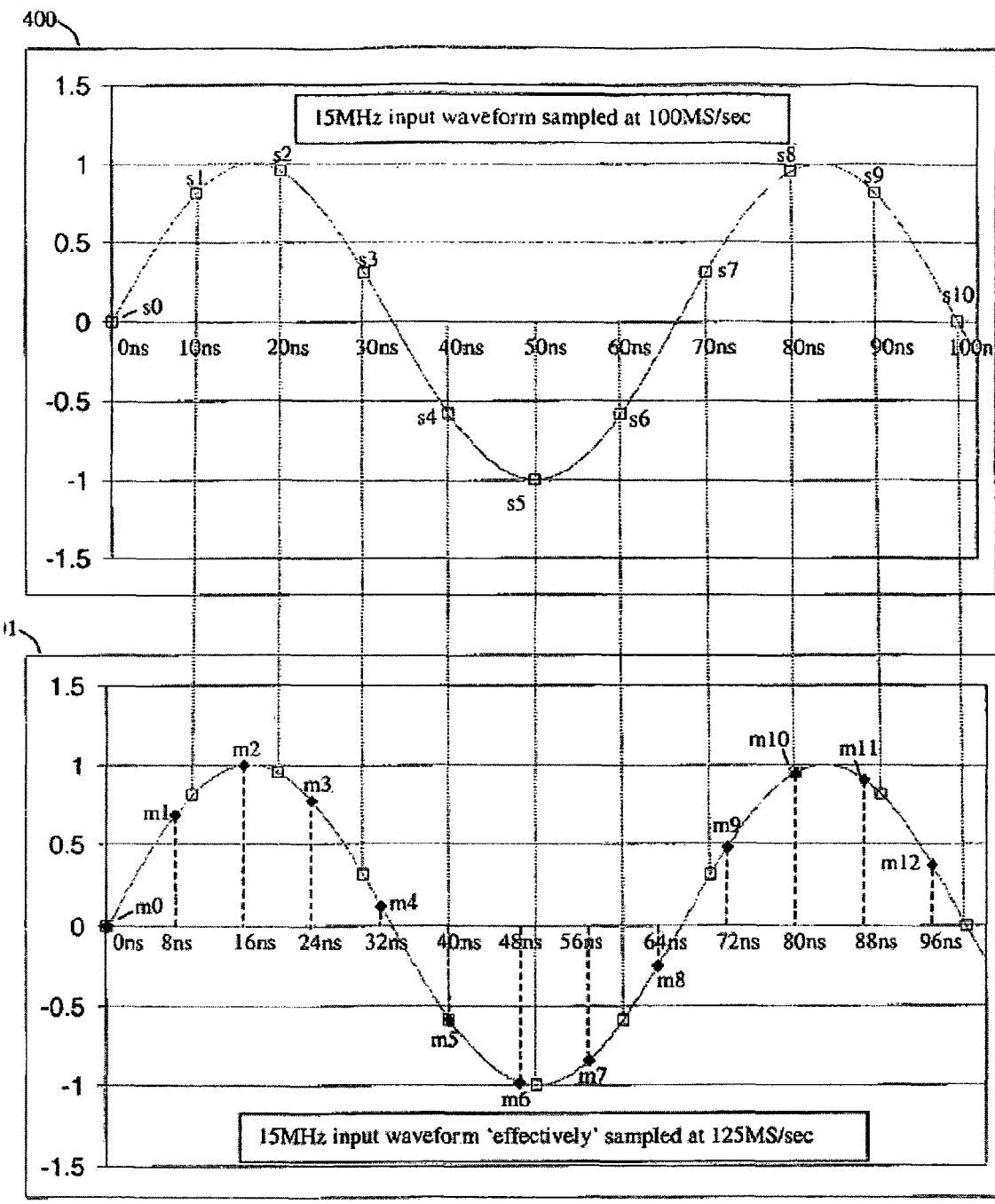
FIGS. 11 and 12 are waveforms applicable to the embodiments of FIG. 10.

FIG. 11 is illustrative of how the function of Sample Rate Adjuster 326 produces an effective sample rate. Points s0 through s10 on waveform 400 represent real sample point measurements of a 15 MHz input signal produced by analog to digital converter 301 that have been stored in RAM 302, subsequently processed by Multiplier 303, and then IIR Filter 304 before being provided as input to Sample Rate Adjuster 326. Waveform 401 consists of effective sample points m0 through m12 that were created by means of Sample Rate Adjuster 326 to appear to be at a higher sample data rate than the real sample data s0 through s10 that it is derived from. Example waveform 401 shown in FIG. 11 results from a Sample Rate Adjust value of 0.8 being loaded into Rate Register 317 of FIG. 10, causing real sample rate data sampled at 100 MS/sec to be converted in to effective sample data of 125 MS/sec. The 100 MS/sec and 125 MS/sec data corresponds to samples s0 through s10 and m0 through m12 respectively. The reference time line increments for waveforms 400 and 401 are 10 ns and 8 ns for 100 MS/sec and 125 MS/sec respectively.

Figure 12:
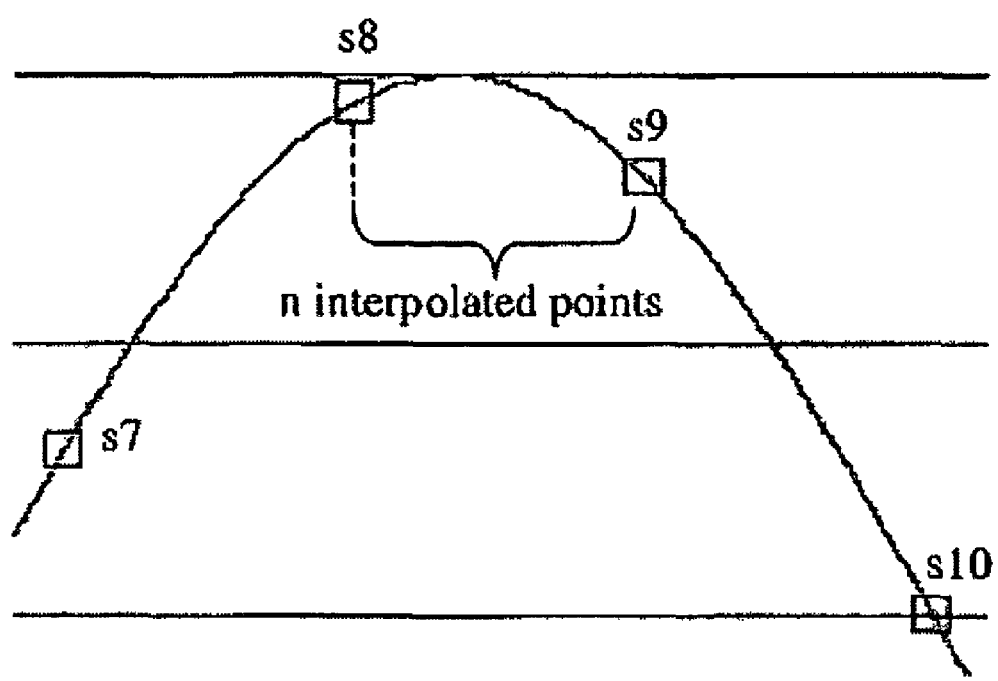

For illustration of how effective sample point amplitudes are determined, FIG. 12 shows an excerpt from waveform 400 of FIG. 11 that contains four contiguous real sample points s7, s8, s9 and s10. The curvature of the line segment that connects s8 and s9 must be accurately interpolated to generate useful effective sample data. The fractional part of the value loaded into Rate Register 317 determines the specific point on the time axis between real sample points s8 and s9 that the amplitude will be calculated for. To this end, sample points s7, s8, s9 and s10 are multiplied by the coefficients a, b, c and d respectively provided by table 319, and then summed by summer 315. Coefficients a, b, c and d from Table 319 are provided to multipliers 308, 310, 312 and 314 respectively. The coefficients are derived for a $4^{th}$ order polynomial to calculate the location of the points that lie on the waveform segment between s8 and s9. A $4^{th}$ order polynomial is only used as an example, as the present inventor recognizes that polynomials of different orders may be used depending on the accuracy required for interpolation.

Thus, the input signal 300 is converted to a digital signal 301a in an A/D 301 and supplied to the RAM 302. The output 302a of the RAM is provided to the multiplier 303 which also receives another input 327 and provides its own output 303a to IIR filter 304 which supplies its initially filtered output 304a to the sample rate adjuster 326.

The sample rate adjuster 326 provides its output 315a to the FIR filter 320, which corresponds to the previously described FIR filter of the prior embodiment. As already noted, the sample rate adjuster 326 changes the number and locations of data points in the original data. To account for that initial data adjustment, the output rate adjuster 321, which receives the FIR filter output 320a produces a readjusted data output 321a, which is based on data provided through input 325a from accumulator 325 and control information 322c from flow control logic 322.

The output 322c is based on information 325b provided from the accumulator 325 to the flow control logic 322, as well as from information 318b, which is provided to flow control logic 322 from accumulator 318, which produces integer based information that is controlled by sample rate adjust parameter 316 provided to the rate register 317 in the form of an output 317a, based further on input 322a from the flow control logic 322. An output rate adjust setting 323 is provided to the rate register 324.

The adjustments provided by the sample rate adjuster 326 are calculated based on coefficient data 319a through d provided from the Table 319 based on the fractional data information 318a provided from the accumulator 318 to the sample rate adjuster 326.

The sample rate adjuster receives the inputs 319a through d and uses those coefficients in conjunction with registers 305, 306 and 307 that provide respective outputs 305a, 306a and 307a, to respective multipliers 310, 312 and 314. Multipliers 308, 310, 312 and 314 produce respective outputs 308a, 310a, 312a and 314a to the summer 315 that produces the aforementioned output 315a.

Ultimately, the circuit block 322 which consists of a rectifier, gates, compressor and A-scan RAM and the like, produces the output for the aforementioned display.

As presented above, FIG. 4 illustrates a first embodiment of a digital tunable filter, and FIGS. 10, 11 and 12 a second embodiment. As described below, FIG. 4b describes a third embodiment which is operable in different modes as described below with reference to FIGS. 4c, 4d, 4e, 4f, 4g and 4h. Sub-blocks that are bypassed or disabled do not appear in these figures in order to make them easier to understand. The sample data rate and data processing rate are shown at each node along the signal processing path and are expressed in the units MS/s and MHz, respectively. Note that FIG. 4b does show all bypass multiplexers (MUX's), enable signals and associated logic.

Figure 4B:
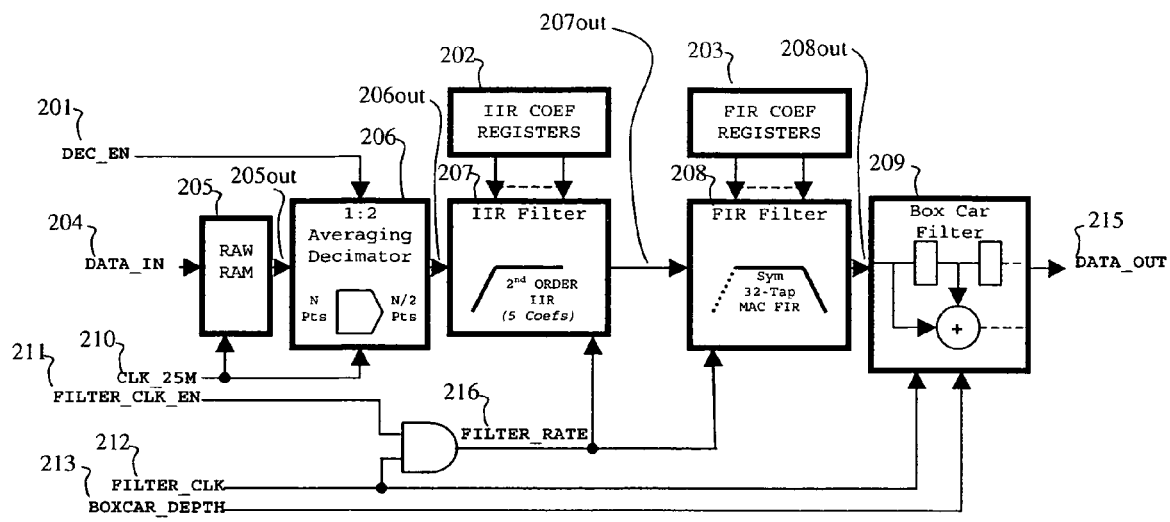
FIG. 4b is block diagram of a further embodiment of a digital tunable filter.
Figure 4B:
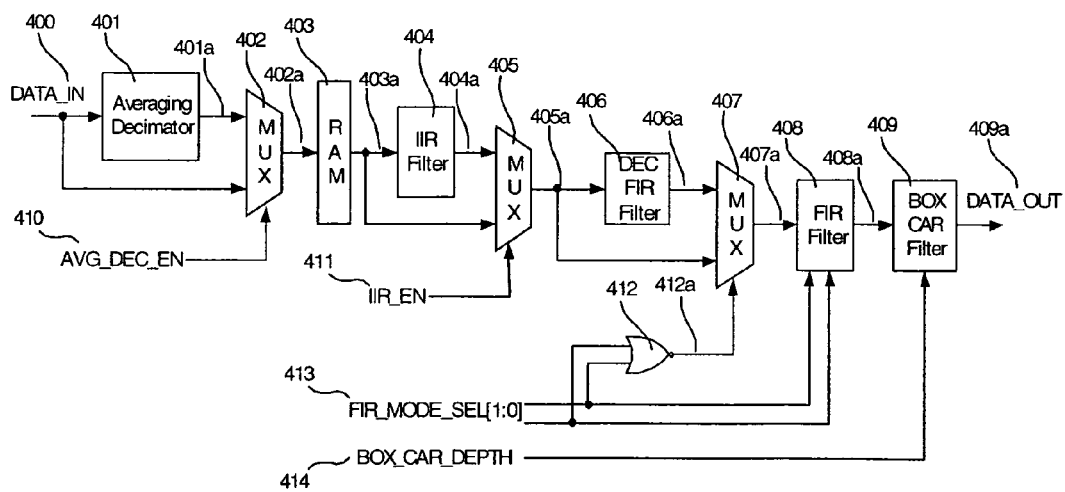

Referring to FIG. 4b, the third embodiment differs in the following ways from the first embodiment described previously relative to FIG. 4:

a) Averaging decimator 401 is located prior to the input of RAM 402, thereby increasing the memory data depth when averaging decimator 401 is enabled. The averaging decimator takes every two contiguous sample points, adds them together, and then divides by two, resulting in one data sample derived from two.

b) Mux's 402, 405 and 407 are used to control the enabling of averaging decimator 401, IIR Filter 404 and FIR Filter 408, respectively. The first embodiment utilizes a different method to enable averaging decimator 206, IIR filter 207 and FIR filter 208 that uses DEC_EN signal 201, FILTER_RATE signal 216 and FILTER_RATE signal 216, respectively.

c) Clock signals are not shown because a global clocking scheme is used. The presence of clock signals is implied, but not explicitly shown. The difference between the depiction of Box Car Filter 209 of FIG. 4 and Box Car Filter 409 is an example of this.

d) FIR Filter 408 switches its coefficients 'on the fly' by time multiplexing the coefficients loaded into a shared set of multipliers.

In FIG. 4b, averaging decimator 401 has same function as that of averaging decimator 206 in FIG. 4 of the first embodiment, except that its location in the signal path is different, as described earlier.

Sample DATA_IN 400 is provided to the input of averaging decimator 401 wherein the average of every pair of contiguous data samples is calculated and provided to its output. Accordingly, the effective sample rate of the output of averaging decimator 401 is one-half that of DATA_IN 400. For example, if DATA_IN 400 was 100 MS/s, the output of averaging decimator 401 would have an effective sample rate of 50 MS/s.

The MUX 402 allows either output 401a of averaging decimator 401 or DATA_IN 400 to be selected as the input provided to RAM 403. MUX 402 is controlled by AVG_DEC_EN signal 410. The RAM 403 has same function as that of RAW RAM 205 in FIG. 4 of the first embodiment.

The purpose of IIR Filter 404 is to provide high pass filtering functions that cannot be realized in FIR Filter 408.

IIR Filter 404 can be switched in and out of the signal path by means of MUX 405 which is controlled by IIR_EN signal 411. This switching capability provides the following two types of band pass filtering methods:

1) Narrow band pass filter (NBPF):
   As shown for the filters of FIGS. 4d and 4f, IIR Filter 404 is bypassed and FIR Filter 408 alone is used for the band pass filtering function.
2) Wide band pass filter (WBPF) and filters with a very low high pass −3 dB corner f frequency:
   As shown for the filters of FIGS. 4c, 4e, 4g and 4h, IIR Filter 404 is used as the high pass filter and FIR Filter 408 is used as the low pass filter.

A primary benefit of this IIR filter design topology is the minimization of required processing speed and digital logic, including multipliers, which would otherwise be required in FIR Filter 408 to achieve comparable filter performance. The benefits of this are lower power and the possibility of using less PCB space due to a smaller FPGA (Field Programmable Gate Array) package size. Both of these benefits allow smaller size and lower material cost.

IIR Filter 404 is based on a $2^{nd}$ order filter using the direct form I realization as is known to those skilled in the art of digital filter design. The only significant difference with respect to this standard realization is that three of the numerator multipliers are replaced by shift registers to approximate the required coefficients. Shift registers require much less gate logic to implement than multiplier functions, hence they are preferable to use in terms of power consumption, miniaturization and lower material cost.

Due to the fact that IIR Filter 404 is only used for high pass filtering, numerator coefficients are needed only to normalize the gain through the filter. The gain error associated with using the aforementioned shift register method can be calculated with substantial accuracy; therefore, the desired overall system gain transfer function can be maintained by selecting the proper coefficients for FIR Filter 408 to compensate for this.

MUX 405 allows either output 404a of IIR Filter 404 or output 403a of RAM 403 to be selected as the input provided to DEC FIR Filter 406. MUX 405 is controlled by IIR_EN signal 411.

The purpose of DEC FIR Filter 406 is to decrease the sample rate of its input data by a factor of two while attenuating frequencies above the Nyquist frequency of its output sample rate. The output of DEC FIR Filter 406 is only used when low frequency narrow band pass filters are required.

A primary benefit of DEC FIR Filter 406 is that it allows minimization of FPGA gate resources in FIR Filter 408 when it is configured as a low frequency narrow band pass filter.

DEC FIR Filter 406 uses, for example, a six tap binary FIR filter with coefficients 1, 0.25, and 0.0625. Binary coefficients allow shift registers to be used in place of multipliers.

The benefits of this are lower power and the possibility of using less PCB space due to a smaller FPGA (Field Programmable Gate Array) package size. Both of these benefits allow smaller size and lower material cost.

DEC FIR Filter 406 low pass filters its input data and then decimates it (i.e. down sampled by 2×) before providing every other sample point to the input of MUX 407.

As is the case with IIR Filter 404, there is a gain error associated with replacing multipliers with shift registers. Advantageously, this error can be calculated with substantial accuracy, and in turn compensated for by selecting proper coefficients for FIR Filter 408.

In operation, data 405a is provided to the input of an anti-aliasing filter (not shown) contained within DEC FIR Filter 406. The output of the anti-aliasing filter is then decimated by passing along every other sample to the output of DEC FIR Filter 406. The anti-aliasing filter is required to prevent frequencies above the new Nyquist frequency from heterodyning into the pass band of the filter.

For example, if input data 405a to DEC FIR Filter 406 is 50 MS/s, its Nyquist frequency will be 25 MHz. The removal of every other data point will create a 25 MS/s effective output sample rate of DEC FIR Filter 406, thereby resulting in a new Nyquist frequency of 12.5 MHz. The anti-aliasing filter located in the first stage of DEC FIR Filter 406 attenuates the frequencies above the 12.5 MHz Nyquist frequency prevent the heterodyning effect described earlier.

MUX 407 allows either output 406a of DEC FIR Filter 406 or output 405a of MUX 405 to be selected as the input provided to FIR Filter 408. MUX 407 is controlled by FIR_MODE_SEL [1.0] signal 413.

The purpose of FIR Filter 408 is to provide low pass filtering, and in some modes of operation, band pass filtering.

Unlike traditional FIR filters, FIR Filter 408 accepts its coefficients 'on the fly' from a set of dedicated registers inside the FPGA. This allows for greater flexibility for user selectable filters.

One innovation associated with FIR Filter 408 is its ability to adjust the effective sample rate of its data. In the present embodiment, FIR Filter 408 is driven by the 100 MHz system clock at all times but is controlled with a system of enables to determine the up-sampling and processing rate of its data. Adjusting the sampling rate of the data provided to the input of FIR Filter 408 is necessary to optimize the Fc/Fs ratio (i.e. the filter cutoff frequency to filter sampling rate) for any given filter. This ratio is a critical factor in determining the stability and effectiveness of FIR Filter 408. The exact limits of this ratio will vary depending on the method and algorithm used to generate the coefficients of FIR Filter 408.

Another innovation used with this design is the time multiplexing of the multipliers used in FIR Filter 408. Using a system of enables (not shown), FIR Filter 408 is able to make use of each multiplier twice in the FIR delay line because it operates at a processing rate that is twice that of the data entering it. This allows one multiplier to be used for two coefficients instead of one, thereby doubling the order of the filter. In this way, the FIR Filter 408 will work as a 65 tap filter, but only use 17 multipliers total (a standard symmetric FIR would use 33). This is a very effective use of FPGA resources that requires FIR Filter 408 to have a minimum up-sample rate of two. Furthermore, input data 407a must be provided to FIR Filter 408 at one half of the desired output sample rate.

BOX CAR Filter 409 has same function as that of BOX CAR Filter 209 in FIG. 4 of the embodiment 1. Specifically, BOX CAR Filter 409 interpolates the data received from the FIR filter in a manner which increases the perceived resolution of the effective sample data by a given factor, preferably by a factor of 4

FIGS. 4c through 4h represent versions of the system shown in FIG. 4b, with, however, the multiplexers and unused sub-blocks removed. These figures are intended to simplify the explanations below of the typical operating modes. It should be noted that the inner workings of each sub-block were described earlier and need not be described again below.

1. Ultra Low Freq Narrow Band Mode [0.2 to 1.2 MHz]

Figures 4C, 4D:
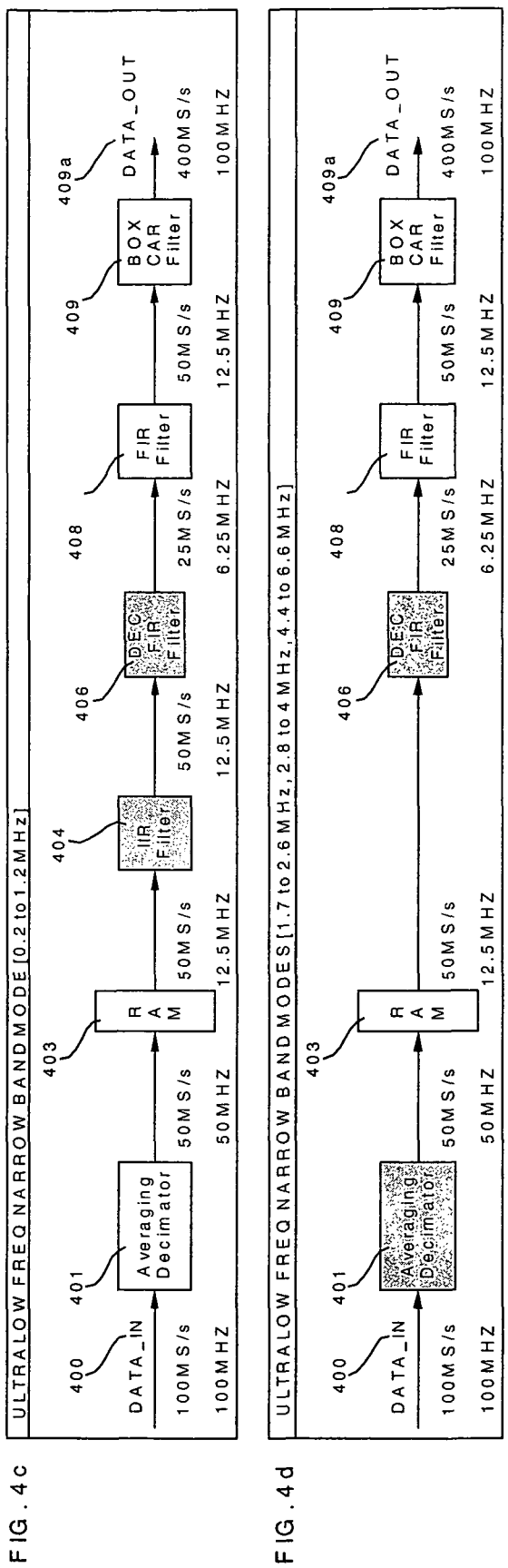
FIGS. 4c, 4d, 4e, 4f, 4g, and 4h are block diagrams of six example filter modes that can be realized with the embodiment of FIG. 4b.

Referring to FIG. 4c, DATA_IN 400 is 100 MS/s sample data provided to the input of Averaging Decimator 401 at a rate of 100 MHz. Averaging Decimator 401 reduces the effective sample rate of its input data to 50 MS/s and provides it to the input of RAM 403 at a rate of 50 MHz for storage. The output of RAM 403 is provided to the input of IIR Filter 404 a rate of 12.5 MHz for high pass filtering. The 50 MS/s output data of IIR Filter 404 is provided to the input of DEC FIR Filter 406 at a rate of 12.5 MHz for anti-alias filtering (not shown) before reducing the effective sample rate of its output data to 25 MS/s. The output of DEC FIR Filter 406 is provided to the input of FIR Filter 408 at a rate of 6.25 MHz for low pass filtering and subsequent up sampling to 50 MS/s before being provided to the input of BOX CAR Filter 409 at a rate of 12.5 MHz. BOX CAR Filter 409 is set to a depth of 8 which converts its input into an output with a 400 MS/s effective sample rate and 100 MHz data transfer rate.

2. Ultra Low Freq Narrow Band Modes [1.7 to 2.6 MHz, 2.8 to 4 MHz, 4.4 to 6.6 MHz]

Referring to FIG. 4d, DATA_IN 400 is 100 MS/s sample data provided to the input of Averaging Decimator 401 at a rate of 100 MHz. Averaging Decimator 401 reduces the effective sample rate of its input data to 50 MS/s and provides it to the input of RAM 403 at a rate of 50 MHz for storage. The output of RAM 403 is provided to the input of DEC FIR Filter 406 at a rate of 12.5 MHz for anti-alias filtering (not shown) before reducing the effective sample rate of its output data to 25 MS/s. The output of DEC FIR Filter 406 is provided to the input of FIR Filter 408 at a rate of 6.25 MHz for low pass and high pass filtering and subsequent up sampling to 50 MS/s before being provided to the input of BOX CAR Filter 409 at a rate of 12.5 MHz. BOX CAR Filter 409 is set to a depth of 8 which converts its input into an output with a 400 MS/s effective sample rate and 100 MHz data transfer rate.

3. Low Freq Narrow Band Mode [0.5 to 4 MHz]

Figures 4E, 4F:
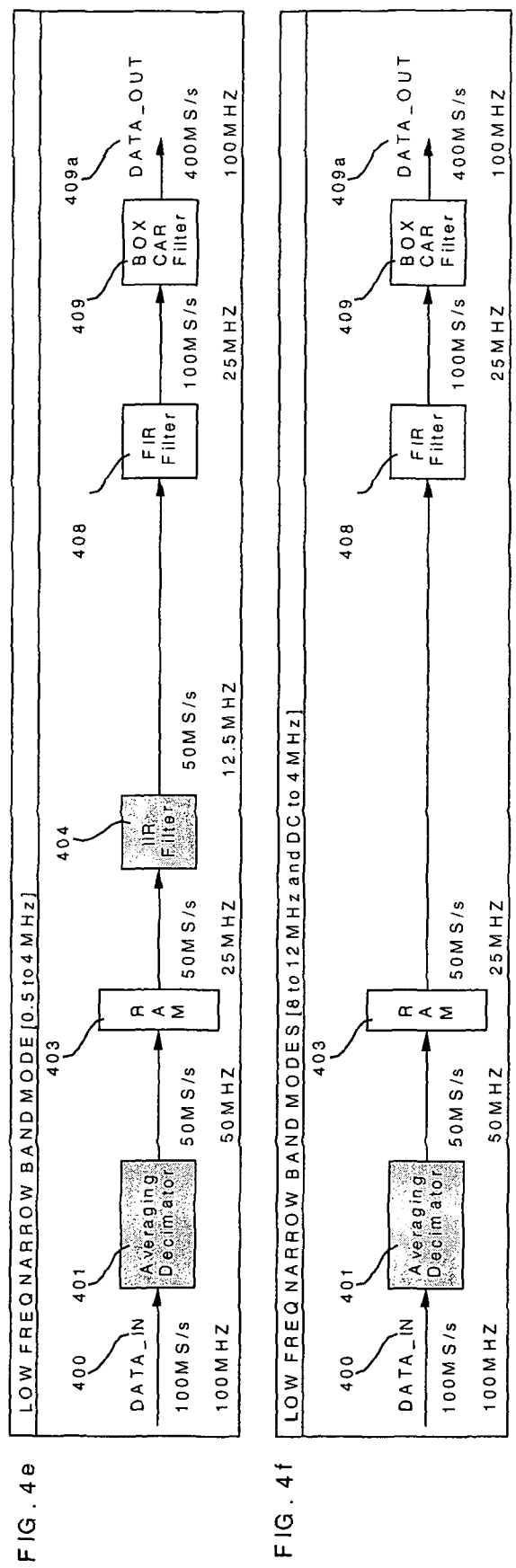

Referring to FIG. 4e, DATA_IN 400 is 100 MS/s sample data provided to the input of Averaging Decimator 401 at a rate of 100 MHz. Averaging Decimator 401 reduces the effective sample data rate of its input data to 50 MS/s and provides it to the input of RAM 403 at a rate of 50 MHz for storage. The output of RAM 403 is provided to the input of IIR Filter 404 at a rate of 25 MHz for high pass filtering. The 50 MS/s output data of IIR Filter 404 is provided to the input of FIR Filter 408 at a rate of 12.5 MHz for low pass filtering and subsequent up sampling to 100 MS/s before being provided to the input of BOX CAR Filter 409 at a rate of 25 MHz. BOX CAR Filter 409 is set to a depth of 4 which converts its input into an output with a 400 MS/s effective sample rate and 100 MHz data transfer rate.

4. Low Freq Narrow Band Mode [DC to 4 MHz 8 to 12 MHz]

Referring to FIG. 4f, DATA_IN 400 is 100 MS/s sample data provided to the input of Averaging Decimator 401 at a rate of 100 MHz. Averaging Decimator 401 reduces the effective sample data rate of its input data to 50 MS/s and provides it to the input of RAM 403 at a rate of 50 MHz for storage. The output of RAM 403 is provided to the input FIR Filter 408 at a rate of 12.5 MHz for low pass and high pass filtering and subsequent up sampling to 100 MS/s before being provided to the input of BOX CAR Filter 409 at a rate of 25 MHz. BOX CAR Filter 409 is set to a depth of 4 to convert its input into an output with a 400 MS/s effective sample rate and 100 MHz data transfer rate.

5. Medium Freq Band Mode [1.5 to 8.5 MHz]

Figures 4G, 4H:
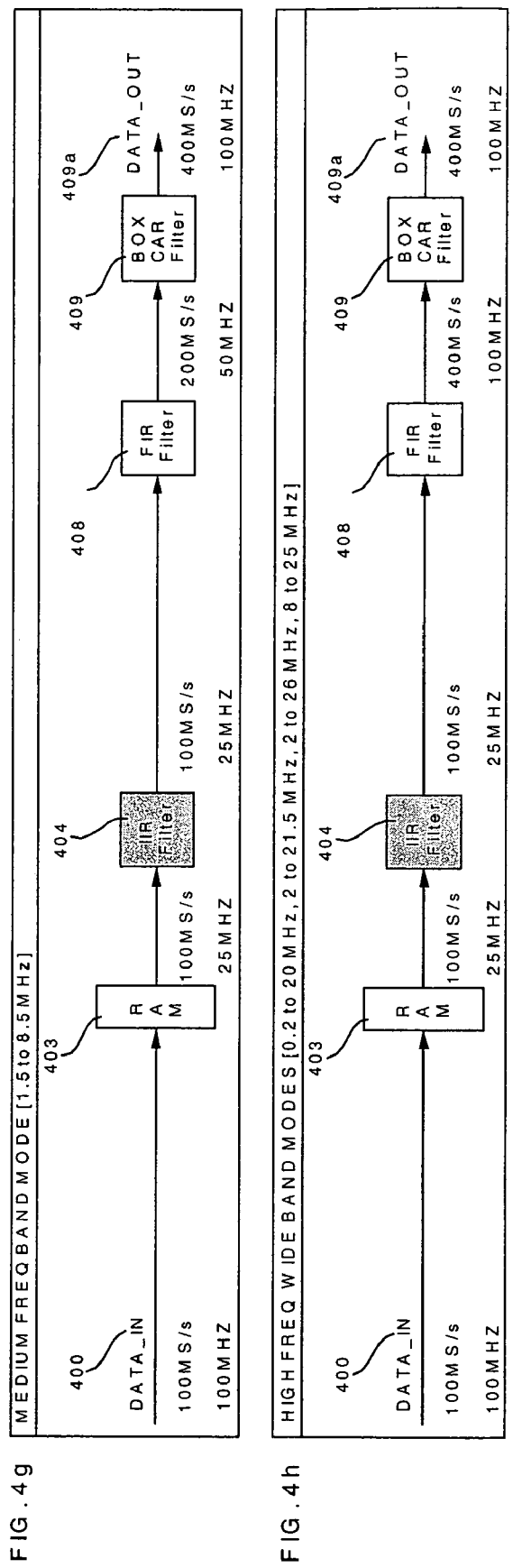

Referring to FIG. 4g, DATA_IN 400 is 100 MS/s sample data provided to the input of RAM 403 at a rate of 100 MHz for storage. The output of RAM 403 is provided to the input of IIR Filter 404 at a rate of 25 MHz for high pass filtering. The output of IIR Filter 404 is provided to the input of FIR Filter 408 at a rate of 25 MHz for low pass filtering and subsequent up sampling to 200 MS/s before being provided to the input of BOX CAR Filter 409 at a rate of 50 MHz. BOX CAR Filter 409 is set to a depth of 2 which converts its input into an output with a 400 MS/s effective sample rate and 100 MHz data transfer rate.

6. High Freq Wide Band Modes [0.2 to 20 MHz, 2 to 21.5 MHz, 2 to 26 MHz, 8 to 25 MHz]

Referring to FIG. 4h, DATA_IN 400 is 100 MS/s sample data provided to the input of RAM 403 at a rate of 100 MHz for storage. The output of RAM 403 is provided to the input of IIR Filter 404 at a rate of 25 MHz for high pass filtering. The output of IIR Filter 404 is provided to the input of FIR Filter 408 at a rate of 25 MHz for low pass filtering and subsequent up sampling to 400 MS/s before being provided to the input of BOX CAR Filter 409 at a rate of 100 MHz. BOX CAR Filter 409 is set to a depth of 1 which converts its input into an output with a 400 MS/s effective sample rate and 100 MHz data transfer rate.

Referring to FIGS. 13 through 16, 'on the fly' coefficient swapping is now further described. This innovation concerns the time multiplexing of the multipliers used in FIR Filter 408 (FIG. 4b). Using a system of enables and selects generated inside Enable Block 1301 (FIG. 13) and illustrated with waveform diagrams in FIG. 16, FIR Filter 408 is able to make use of each Multiplier 1403 (FIG. 14) twice in the FIR delay line because it operates at a processing rate that is twice that of the sample data entering it.

Figure 13:
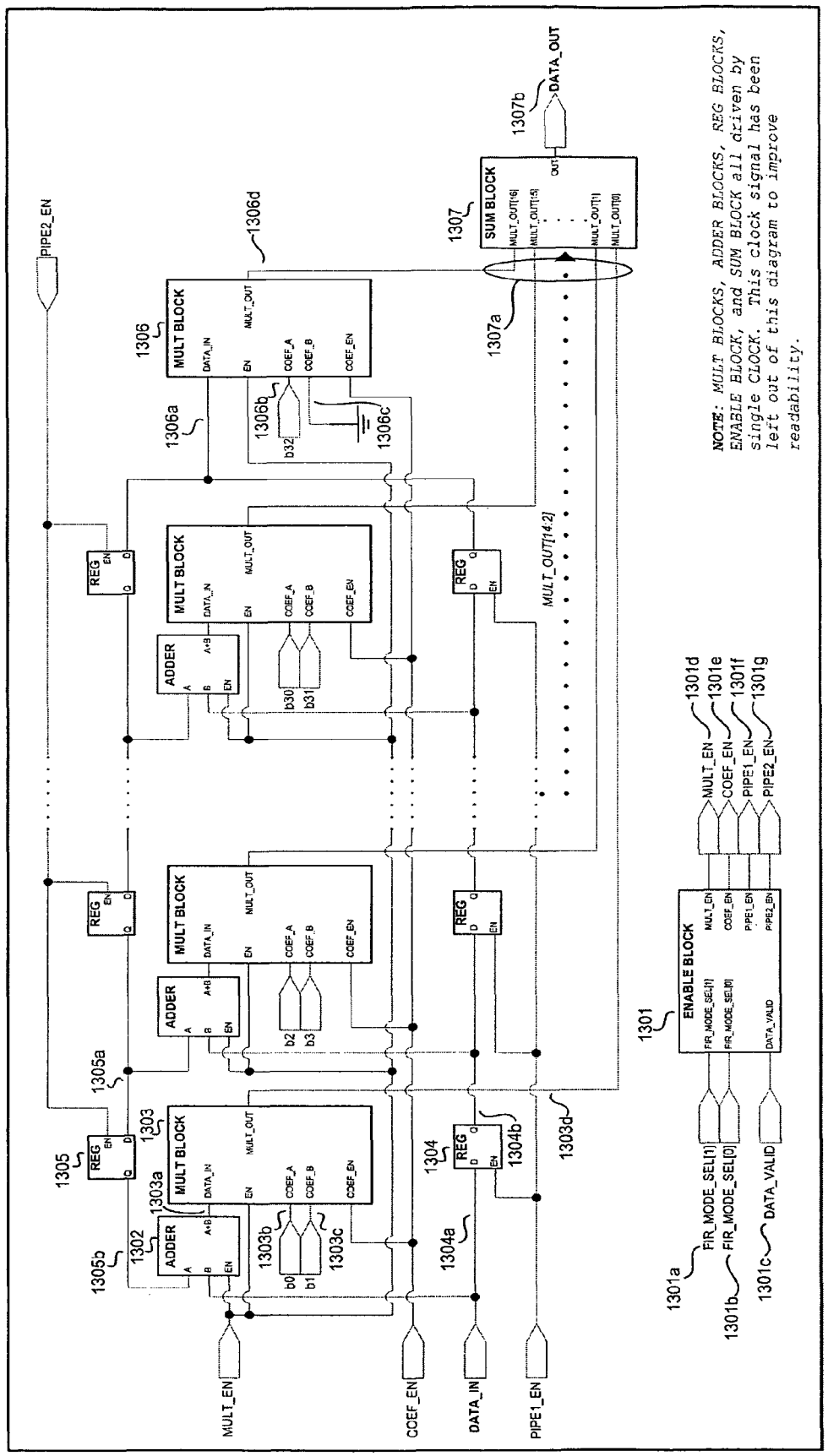
FIG. 13 is a block diagram of the FIR Filter component of FIG. 4b.
Figure 14:
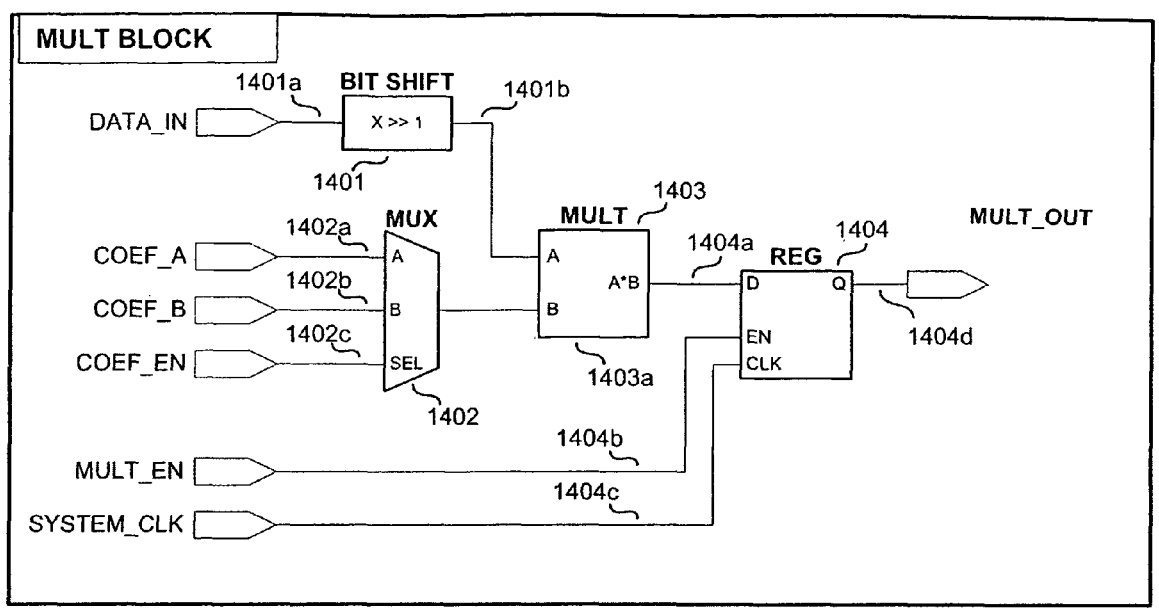
FIG. 14 is a block diagram of the mult block component of FIG. 13.
Figure 15:
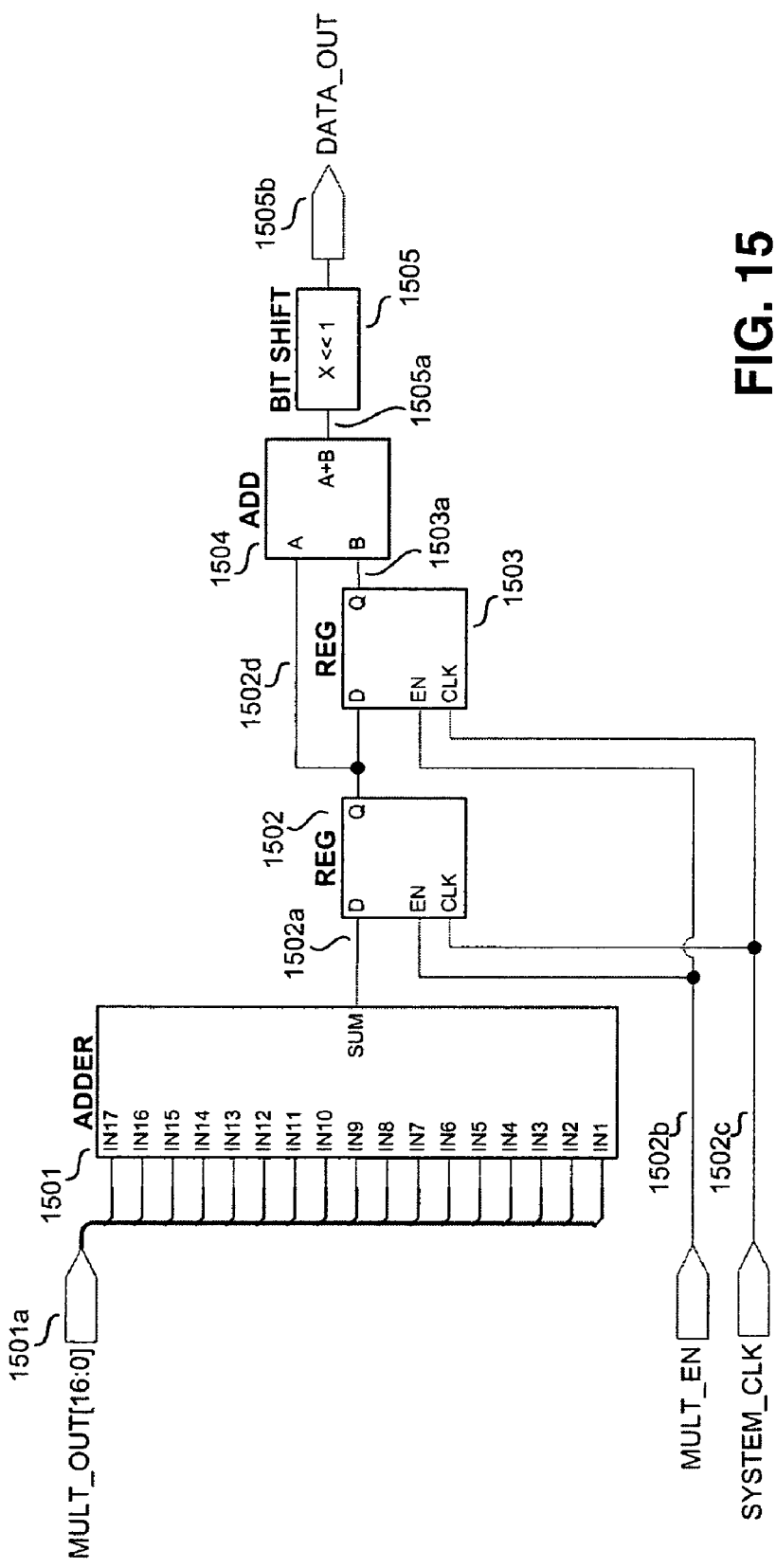
FIG. 15 is a block diagram of the sum block component of FIG. 13.
Figure 16:
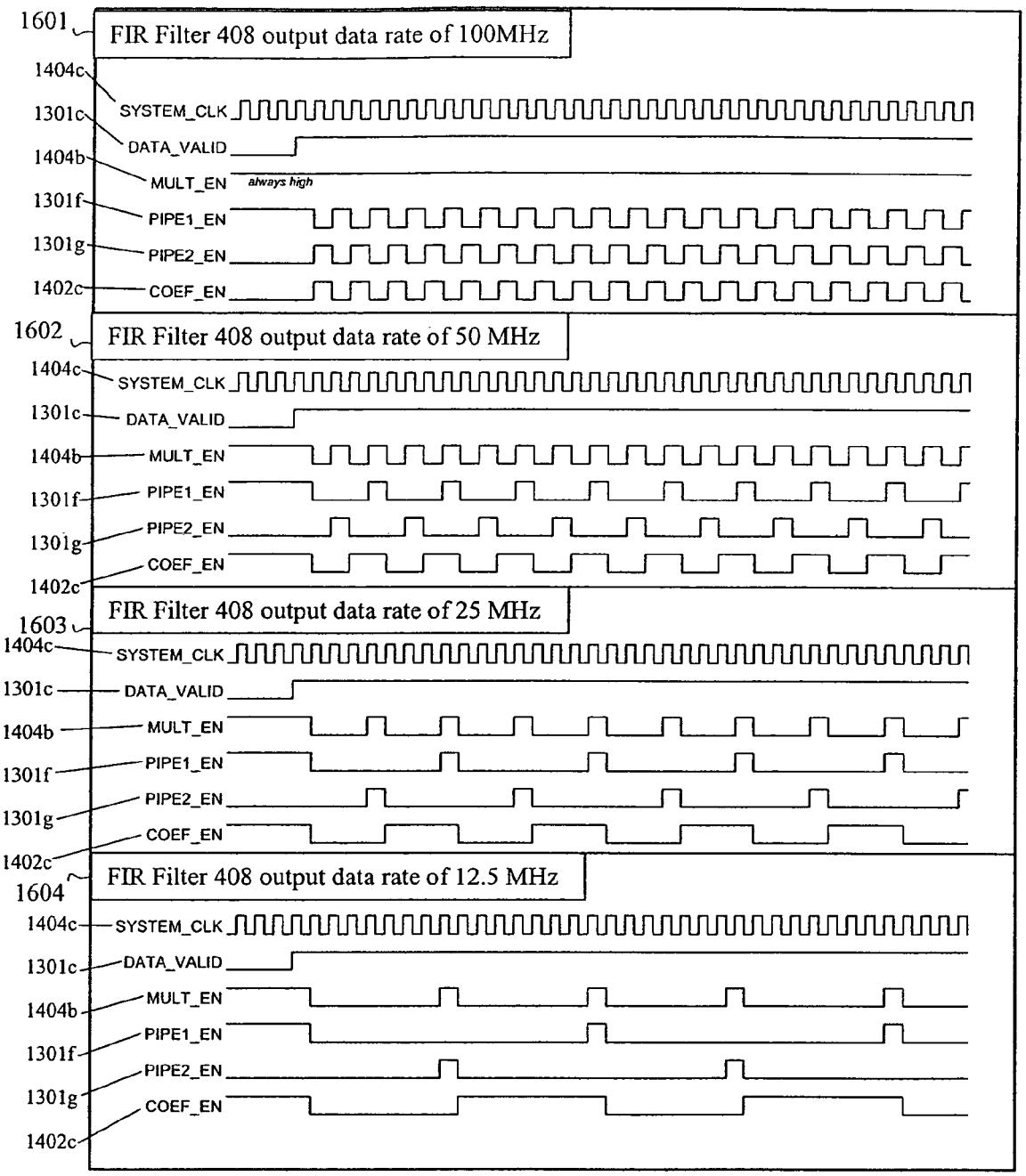
FIG. 16 shows the timing diagrams associated with the operating modes of FIR Filter shown in FIG. 13.

Multiplier sections contained within FIR Filter 408 are shown in FIG. 13. With the exception of MULT_BLOCK 1306, an odd and an even coefficient is provided, respectively, to the COEF_A and COEF_B input of each MULT_BLOCK. In the case of MULT_BLOCK 1306, even coefficient b32 is provided to the COEF_A input and the input to the COEF_B input is set permanently to all zeros. COEF_A and COEF_B are selected dynamically by means of COEF_EN 1402c. The MULT_OUT signal of each MULT_BLOCK is updated with the product of newly multiplied data whenever MULT_EN is high and the rising edge of SYSTEM_CLK 1404c occurs.

When FIR Filter 408 has an output data rate of 12.5 MHz, 25 MHz and 50 MHz (shown in 1604, 1603 and 1602 of FIG. 16, respectively), the product of newly multiplied data is provided to MULT_OUT at a rate of ⅛, ¼ and ½ of the rate of SYSTEM_CLK 1404c, respectivley. In the case when FIR Filter 408 has an output data rate of 100 MHz (1601 of FIG. 16), newly multiplied data is provided to MULT_OUT at the same rate as SYSTEM_CLK 1404c because MULT_EN is always high.

In all output data rate cases of FIR Filter 408 alternate coefficients are used for each multiplier cycle, allowing one Multiplier 1403 to be used for two coefficients instead of one, thereby doubling the order of the filter. A customized Summing Block 1307 (shown in detail in FIG. 15) is then used to correctly assemble these phase-shifted halves of each output data point.

In this way, the FIR Filter 408 will work as a 65 tap filter, but only use 17 multipliers total (a standard symmetric FIR would use 33). This is a very efficient use of FPGA resources that requires FIR Filter 408 to have a minimum up-sample rate of two. Furthermore, input data 407*a* must be provided to FIR Filter 408 at one half of the desired output sample rate.

Throughout the specification and claims, reference is made to "echo" signals. As will be appreciated by people of skill in the art, in certain environments or applications, the transmitter and receiver components of the transducer 12 are physically separated, with the receiver being located on an opposite side of the object being tested. Hence, the term "echo" as used herein also pertains and encompasses embodiments where the so-called echo signal passes through the object being tested.

In the preceding description, the invention that has been described exclusively with respect to embodiments wherein flaw detection is carried out with a single transducer element operating exclusively under the echo principle and/or by reference to a transmitter/receiver pair which handle ultrasound waves that pass through a material. However, it should be noted the present invention is equally applicable to flaw detection instruments that use an array of transducer elements, such as an ultrasonic phased array probe. As is the case with a single element ultrasonic transducer, the response signal for each transducer element of the phased array ultrasonic probe used for reception is provided to the input of a receiver channel for conditioning and subsequent digitization by an analog to digital converter. In other words, the reference in the claims to a "transducer"—in the singular—is deemed to pertain to an ultrasonic phased array type of a probe as well. Such arrays of transducers are deemed to be either identical or at least equivalent to a single element transducer. The structure of such ultrasonic phased array devices is described or referenced in U.S. Pat. Nos. 4,497,210 and 6,789,427, the contents of which patents are incorporated herein by reference.

Although the present and alternate inventions have been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An ultrasonic detection system for scanning objects to be tested, the system comprising:
a transmit and receive device to generate a test signal and to receive a responsive echo signal;
a transducer that converts the test signal to an ultrasonic signal, applies the ultrasonic signal to a target object to be tested, receives an ultrasonic echo signal and produces the echo signal for the transmit and receive device;
a signal processing circuit coupled with the transmit and receive device for receiving and processing the echo signal, the signal processing circuit including at least one analog to digital converter for converting an analog version of the echo signal to a digital echo signal comprising streaming digital data obtained at a first sample rate and associated with a first data rate; and
a digital tuner circuit including:
a first circuit section which is structured to receive the streaming digital data;
a second circuit section coupled with the first circuit section and structured to process the streaming digital data at a second data rate which is slower than the first data rate and further structured to create from the streaming digital data intermediate streaming data having a second sample rate; and
a third circuit section responsive to the second circuit section to create final streaming digital data representative of the echo signal and characterized by having a third sample rate which is outputted at a third data rate, wherein the third data rate is higher than the first data rate, the third circuit section being configured to produce the third data rate by interpolating the intermediate streaming data to increase the perceived resolution of the streaming digital data by a predetermined factor.

2. The system of claim 1, wherein the second sample rate is lower than the first sample rate.

3. The system of claim 1, wherein the first circuit section comprises a memory in which the streaming digital data is capable of being stored at the first data rate, wherein the second circuit section includes an infinite impulse response (IIR) filter that processes data from the memory and provides an output data to a finite impulse response (FIR) filter, for applying a frequency filtering function to the data, and wherein the third circuit section comprises a box car filter which processes data received from the FIR filter in a manner which increases the perceived resolution of the data by a predetermined factor.

4. The system of claim 1, wherein the first circuit section comprises an averaging decimator which receives the streaming digital data and from which the intermediate streaming digital data is provided at a sample rate lower than the first sample rate.

5. The system of claim 4, wherein the second circuit section includes a finite impulse response (FIR) filter.

6. The system of claim 4, wherein the second circuit section further includes an infinite impulse response (IIR) filter for applying a frequency filtering function to the streaming digital data.

7. The system of claim 4, further including a decimating FIR filter.

8. The system of claim 1, including an averaging decimator and a memory, and wherein the first circuit section is selectively configurable as either the averaging decimator or as the memory.

9. The system of claim 8, wherein the second circuit section includes an FIR filter, an optionally selectable IIR filter and an optionally selectable decimating FIR filter.

10. The system of claim 9, wherein the third circuit section comprises a box car filter which processes data received from the second circuit section, in a manner which increases the perceived resolution of the data by a predetermined factor.

11. The system of claim 2, in which the predetermined factor is equal to four.

12. The system of claim 3, further including an averaging decimator coupled to the memory for reducing the number of data samples that are being provided to the IIR filter.

13. The system of claim 3, wherein the second data rate is one-fourth the first data rate.

14. The system of claim 3, wherein the FIR filter is set to provide a frequency selectivity response which provides a −6 dB low pass filter point which is less than 10% of a filter clock applied thereto and which determines the third data rate.

15. The system of claim 3, including an inputting circuit that enables a user to set a band pass response for the FIR filter, by providing operator settable values.

16. The system of claim 3, wherein the FIR filter and the IIR filter operate synchronously.

17. The system of claim 3, includes means for playing back sample data from the memory at one-fourth its original data rate and processing the data that has been stored in the memory to achieve a data rate four times as large as the original data rate.

18. The system of claim 3, wherein the FIR filter is a symmetrical 32 tap MAC filter with 32 coefficients, which are based on only sixteen values used with no more than sixteen digital hardware multipliers.

19. The system of claim 3, including means that enable an operator to select from numerous fLPF−6 dB points.

20. The system of claim 3, wherein the IIR filter utilizes five IIR filter coefficients which are calculated at least in part by reference to a −3 dB cutoff correction factor, a desired −3 dB cut off frequency, and a corrected −3 dB cutoff frequency.

21. The system of claim 20, wherein the FIR filter is programmable by a user to specify −6 dB roll off points for either a low pass or a band pass filter function.

22. The system of claim 3, wherein the box car filter is structured to produce a rolling average of variable depth of data which is received by the box car filter.

23. The system of claim 3, wherein a −6 dB setting for the FIR filter is selectable in the range from about 0.1 to about 25 MHz.

24. The system of claim 1, wherein the system comprises an ultrasonic test instrument.

25. The system of claim 1, wherein the system comprises and eddy current test instrument.

26. The system of claim 1, in which the data in the first circuit section is received in a burst mode.

27. The system of claim 26, in which the burst mode is periodic and endures for approximately twenty percent of the period of each cycle.

28. The system of claim 1, the first circuit section including an averaging decimator, coupled between at least one analog to digital converter and a memory of the digital tuner circuit, for processing the streaming digital data prior to its storage in the memory.

29. The system of claim 28, further including a first selection circuit located between the averaging decimator and the memory for enabling selective supplying to the memory of either the streaming digital data supplied from the at least one analog to digital converter, or an output of the averaging decimator.

30. The system of claim 28, further including a second selection circuit coupled between the memory and the FIR filter, for enabling selective bypassing of the IIR filter.

31. The system of claim 30, further including a decimating FIR filter coupled between the first selection circuit and the FIR filter.

32. The system of claim 31, further including a third selection circuit coupled between the decimating FIR filter and the FIR filter.

33. The system of claim 28, wherein the FIR filter is structured to switch its coefficients dynamically.

34. The system of claim 32, in which the digital tuner circuit is operable in a plurality of selectable operation modes.

35. The system of claim 34, in which the selectable operation modes include:
a. ultra low frequency narrow band mode of 0.2 to 1.2 MHz;
b. ultra low frequency narrow band modes of 1.7 to 2.6 MHz, 2.8 to 4 MHz and 4.4 to 6.6 MHz;
c. low frequency narrow band mode of 0.5 to 4 MHz;
d. low frequency narrow band mode of 0 to 4 MHz and 8 to 12 MHz;
e. medium frequency band mode of 1.5 to 8.5 MHz; and
f. high frequency wide band modes of 0.2 to 20 MHz, 2 to 21.5 MHz, 2 to 26 MHz and 8 to 25 MHz.

* * * * *